US011786184B2

(12) United States Patent
Kano et al.

(10) Patent No.: US 11,786,184 B2
(45) Date of Patent: Oct. 17, 2023

(54) MEDICAL INFORMATION DISPLAY APPARATUS

(71) Applicant: Canon Medical Systems Corporation, Otawara (JP)

(72) Inventors: Yusuke Kano, Nasushiobara (JP); Anri Sato, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 586 days.

(21) Appl. No.: 16/552,300

(22) Filed: Aug. 27, 2019

(65) Prior Publication Data

US 2020/0069259 A1 Mar. 5, 2020

(30) Foreign Application Priority Data

Aug. 30, 2018 (JP) .................................. 2018-161579
Aug. 23, 2019 (JP) .................................. 2019-153059

(51) Int. Cl.
*A61B 5/00* (2006.01)
*G16H 15/00* (2018.01)
*G16H 30/20* (2018.01)
*G16H 10/60* (2018.01)

(52) U.S. Cl.
CPC ............ *A61B 5/7435* (2013.01); *A61B 5/743* (2013.01); *G16H 15/00* (2018.01); *G16H 30/20* (2018.01); *A61B 5/7465* (2013.01); *G16H 10/60* (2018.01)

(58) Field of Classification Search
None
See application file for complete search history.

(56) References Cited

U.S. PATENT DOCUMENTS

| | | | | |
|---|---|---|---|---|
| 6,415,164 | B1 * | 7/2002 | Blanchard | H04M 1/72469 |
| | | | | 455/566 |
| 8,434,020 | B2 * | 4/2013 | Martyn | H04M 1/72469 |
| | | | | 715/808 |
| 8,645,299 | B2 * | 2/2014 | Faughnan | G16H 10/60 |
| | | | | 600/300 |
| 9,730,648 | B2 * | 8/2017 | Kassem | A61B 5/021 |
| 10,032,236 | B2 * | 7/2018 | Hawkins | G16H 15/00 |

(Continued)

FOREIGN PATENT DOCUMENTS

| | | |
|---|---|---|
| JP | 2009-104278 A | 5/2009 |
| JP | 2014-206834 A | 10/2014 |

(Continued)

OTHER PUBLICATIONS

Office Action dated Aug. 1, 2023, issued in corresponding Japanese patent application No. 2019-153059.

*Primary Examiner* — Mallika D Fairchild
(74) *Attorney, Agent, or Firm* — Oblon, McClelland, Maier & Neustadt, L.L.P.

(57) ABSTRACT

According to one embodiment, a medical information display apparatus includes processing circuitry. The processing circuitry displays first medical information over a first period along a first time axis and second medical information over a second period along a second time axis, acquires time information at a time point or in a range designated in the first period about the first medical information displayed, decides a position on the second time axis which corresponds to the time information, and displays an indicator indicating the position in an area displaying the second medical information.

13 Claims, 19 Drawing Sheets

(56) References Cited

U.S. PATENT DOCUMENTS

| | | | | |
|---|---|---|---|---|
| 10,271,798 B2* | 4/2019 | Kassem | ................ | A61B 5/743 |
| 10,303,850 B2* | 5/2019 | Kurami | ............... | G06F 16/2477 |
| 10,446,270 B2* | 10/2019 | Tsugo | ................... | G16H 40/63 |
| 10,806,407 B2* | 10/2020 | Utsunomiya | .......... | G16H 40/63 |
| 10,987,065 B2* | 4/2021 | Qing | .................... | A61B 5/7445 |
| 11,037,662 B2* | 6/2021 | Qing | ................... | G06F 3/04847 |
| 2007/0176931 A1* | 8/2007 | Tivig | ..................... | G16H 40/63 |
| | | | | 345/440 |
| 2011/0161269 A1* | 6/2011 | Faughnan | .............. | G16H 10/60 |
| | | | | 707/E17.093 |
| 2011/0245629 A1* | 10/2011 | Giftakis | ............... | A61B 5/4094 |
| | | | | 600/301 |
| 2014/0022256 A1* | 1/2014 | Carnes | ............... | A61B 5/14553 |
| | | | | 345/440.1 |
| 2014/0218368 A1* | 8/2014 | Hatano | ................. | G16H 40/63 |
| | | | | 345/440 |
| 2014/0275819 A1* | 9/2014 | Kassem | ............ | A61B 5/14551 |
| | | | | 600/301 |
| 2015/0248534 A1* | 9/2015 | Krzywicki | ............ | G06F 3/0482 |
| | | | | 715/771 |
| 2017/0014090 A1* | 1/2017 | Tsugo | ................... | G06Q 10/10 |
| 2017/0017764 A1* | 1/2017 | Tsugo | ................... | G16H 40/63 |
| 2018/0263575 A1* | 9/2018 | Qing | ...................... | G16Z 99/00 |
| 2018/0277243 A1* | 9/2018 | Qing | ..................... | A61B 5/339 |
| 2019/0029610 A1* | 1/2019 | Utsunomiya | ........ | A61B 5/7425 |
| 2019/0066827 A1* | 2/2019 | Noro | ...................... | G16H 30/20 |
| 2020/0121199 A1* | 4/2020 | Freeman | .................. | G06F 3/14 |

FOREIGN PATENT DOCUMENTS

| | | |
|---|---|---|
| JP | 2015-197736 A | 11/2015 |
| JP | 2017-162122 A | 9/2017 |
| WO | 2008/013193 A1 | 1/2008 |

\* cited by examiner

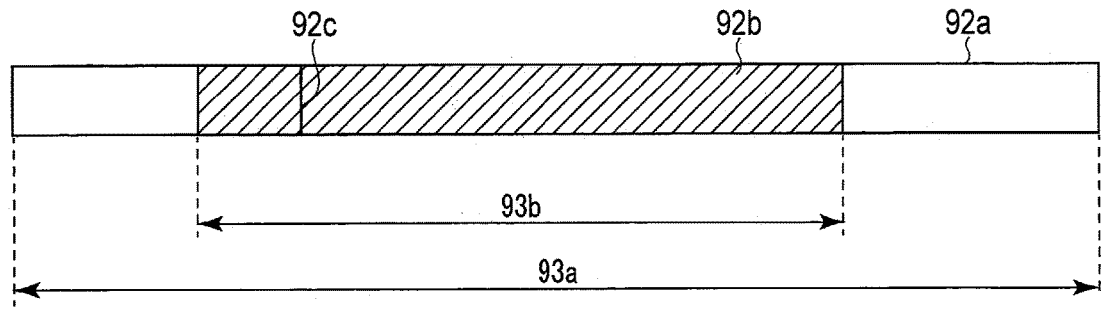
F I G. 9
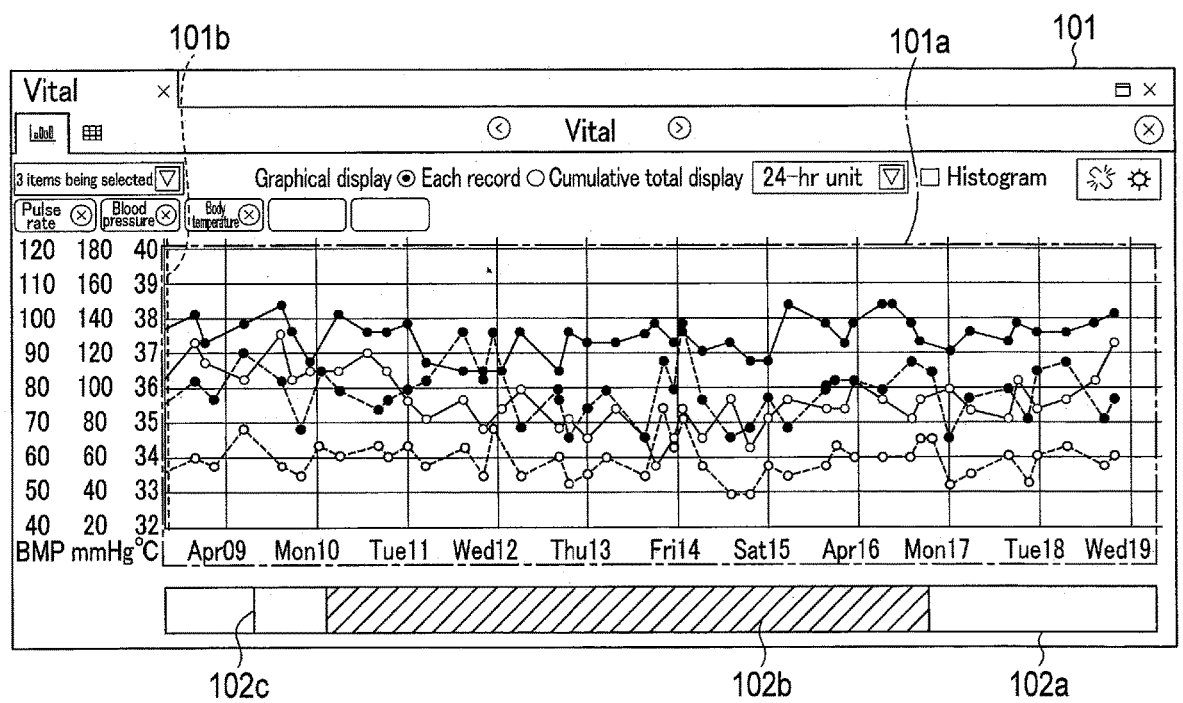
F I G. 10

F I G. 17

| | 2017-03-03 19:00 | 2017-04-06 03:04 | 2017-04-07 18:00 | 2017-04-12 20:13 | 2017-04-15 18:47 | 2017-04-18 22:17 | 2017-04-20 18:22 | 2017-04-24 18:47 |
|---|---|---|---|---|---|---|---|---|
| Blood count(Blood) | | | | | | | | |
| Hb (Blood) | 12.1g/dL | 12.5g/dL | 12.2g/dL | 12.8g/dL | 12.9g/dL | 12.7g/dL | 12.6g/dL | 12.7g/dL |
| RBC(Blood) | 488×10^4/μL | 500×10^4/μL | 486×10^4/μL | 505×10^4/μL | 508×10^4/μL | 495×10^4/μL | 498×10^4/μL | 497×10^4/μL |
| Hct(Blood) | 35% | 36.6% | 36.6% | 37.3% | 38.2% | 37.7% | 37.6% | 37.9% |
| MCV(Blood) | 71.7fL | 73.2fL | 75.3fL | 73.9fL | 75.2fL | 76.2fL | 75.5fL | 75.4fL |
| MCH(Blood) | 24.8Pg | 25Pg | 25.1Pg | 25.3Pg | 25.4Pg | 25.7Pg | 25.3Pg | 25.2Pg |

F I G. 18

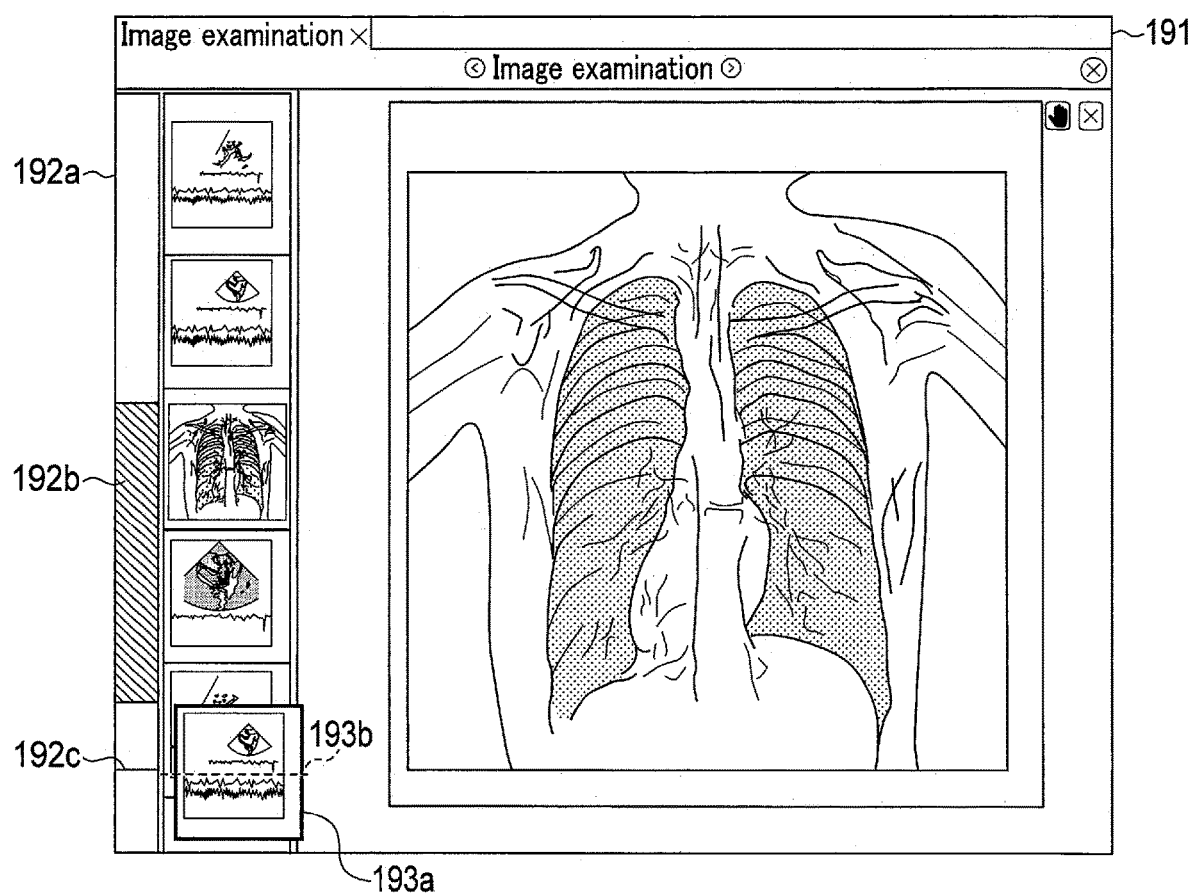
F I G. 19

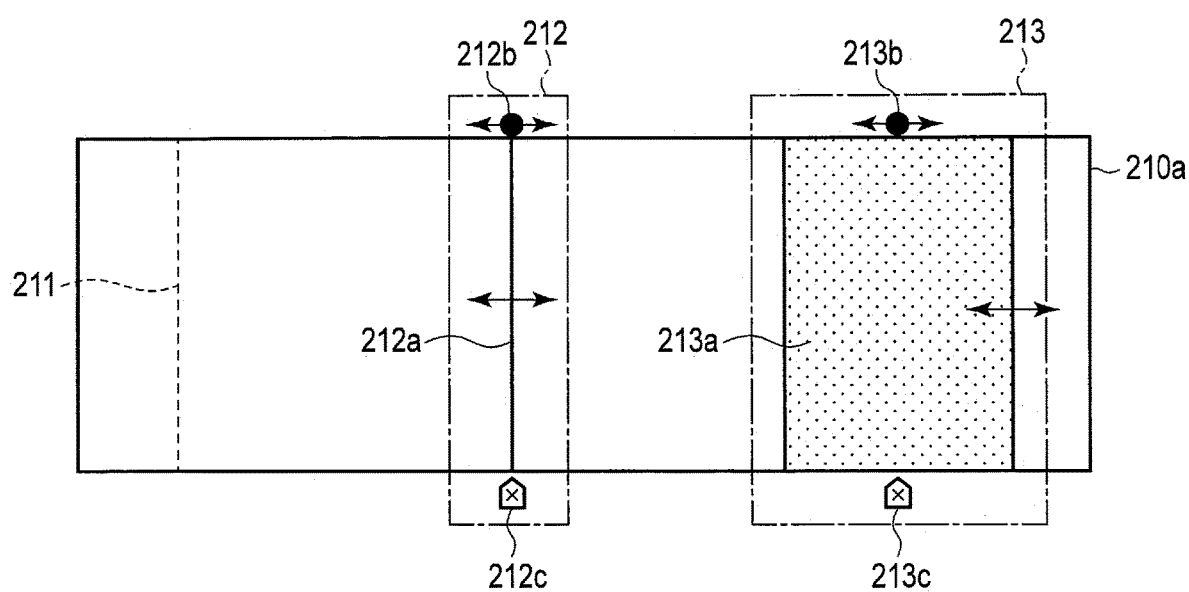
F I G. 21

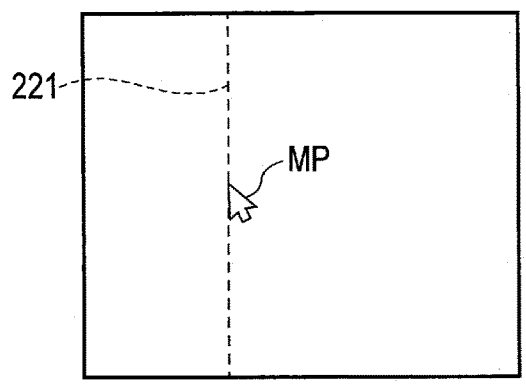
F I G. 22A
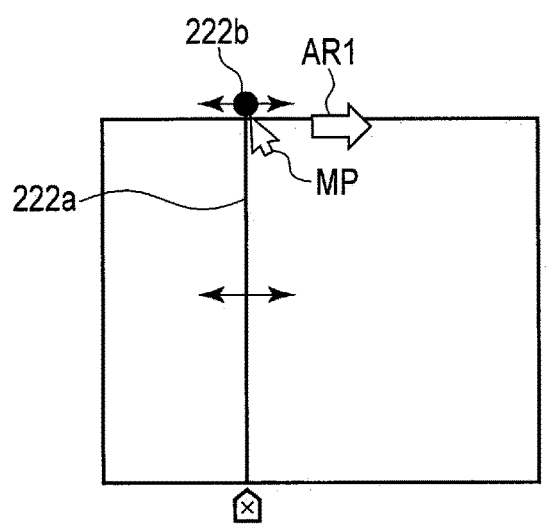
F I G. 22B
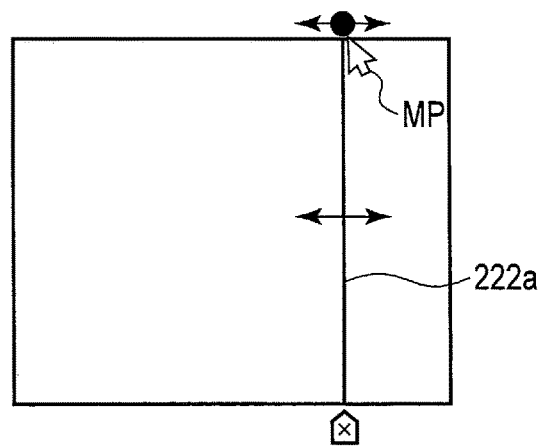
F I G. 22C

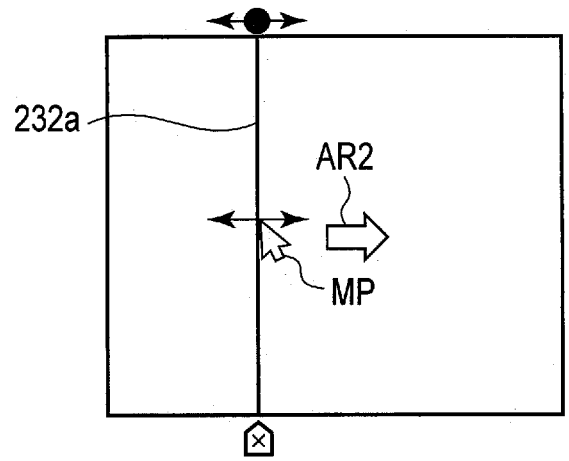
F I G. 23A
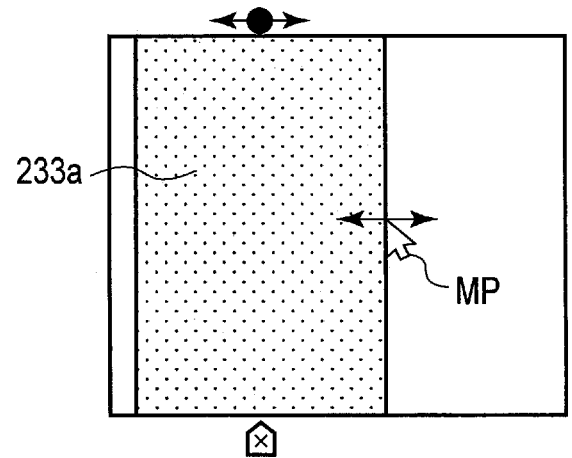
F I G. 23B

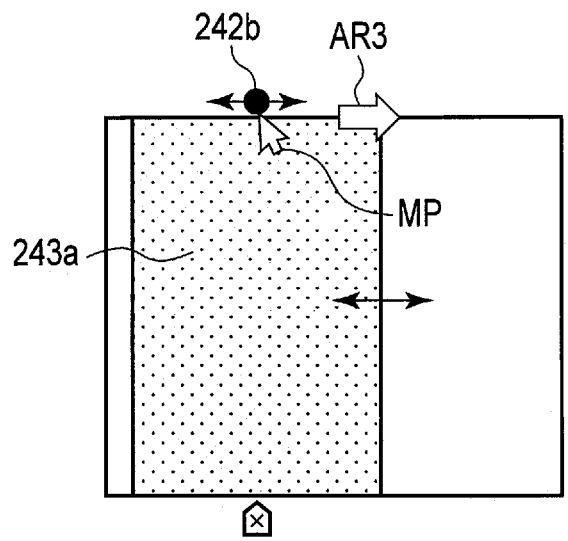
F I G. 24A
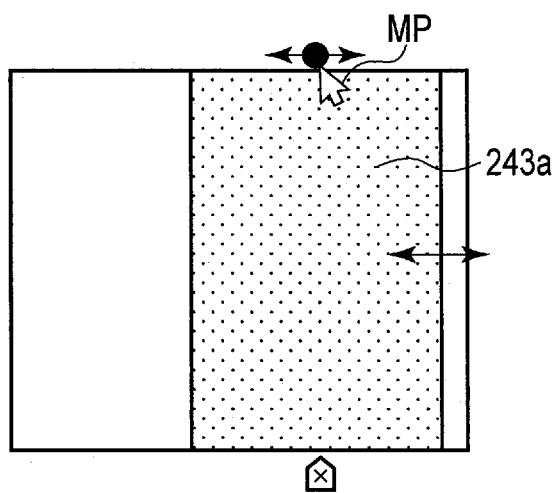
F I G. 24B

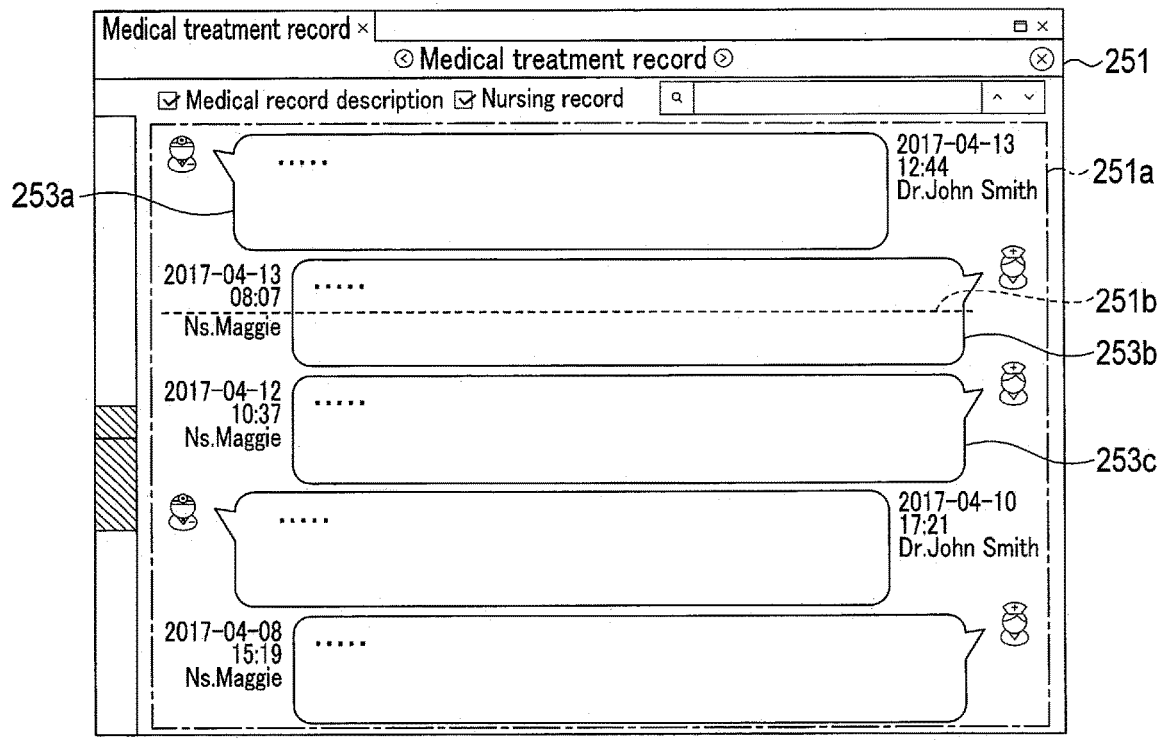
F I G. 25
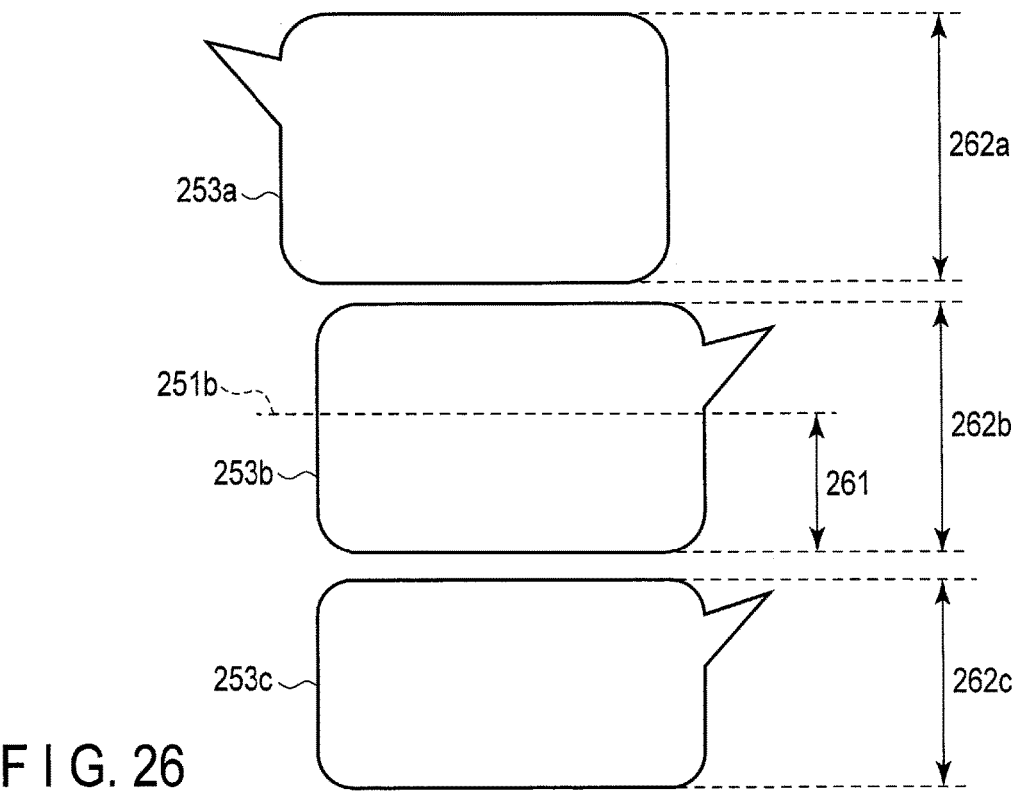
F I G. 26

MEDICAL INFORMATION DISPLAY APPARATUS

CROSS-REFERENCE TO RELATED APPLICATIONS

This application is based upon and claims the benefit of priority from Japanese Patent Applications No. 2018-filed Aug. 30, 2018; and No. 2019-153059, filed Aug. 23, 2019; the entire contents of both of which are incorporated herein by reference.

FIELD

Embodiments described herein relate generally to a medical information display apparatus.

BACKGROUND

There are demands for a medical information display apparatus that displays, on one screen, various types of medical treatment data required for a doctor to make diagnosis and examine a medical treatment policy.

There is known a medical information display apparatus in which operating parts for receiving the designation of dates are provided for a plurality of panels respectively corresponding to a plurality of medical treatment data to automatically display, upon designation of a date, information about the selected date on another panel.

This medical information display apparatus does not allow any check on associated data until automatic display switching processing for dates. If, therefore, a selected date and time do not coincide with a desired date and time, the preceding display contents may be lost.

Accordingly, the conventional medical information display apparatus suffers from the problem that the association between medical information displayed in a plurality of areas is difficult to understand.

BRIEF DESCRIPTION OF THE DRAWINGS

FIG. 9 shows an example of the arrangement of the navigation area according to the embodiment;

FIG. 10 is a view showing another display example of the vital sign information area including the navigation area according to the embodiment;

FIG. 17 is a view showing a display example of a specimen examination information area including a preview area according to the embodiment;

FIG. 18 is a view showing a display example of a medical treatment record information area including a preview area according to the embodiment;

FIG. 19 is a view showing a display example of an image information area including a preview area according to the embodiment;

FIG. 21 is a view showing a display example of indicators according to the embodiment;

FIG. 22A is a view exemplarily showing an indicator moving method according to the embodiment;

FIG. 22B is a view exemplarily showing an indicator moving method according to the embodiment;

FIG. 22C is a view exemplarily showing an indicator moving method according to the embodiment;

FIG. 23A is a view exemplarily showing an indicator range selection method according to the embodiment;

FIG. 23B is a view exemplarily showing an indicator range selection method according to the embodiment;

FIG. 24A is a view exemplarily showing an indicator moving method upon range selection according to the embodiment;

FIG. 24B is a view exemplarily showing an indicator moving method upon range selection according to the embodiment;

FIG. 25 is a view showing a display example of a medical treatment record information area where an indicator is displayed on a comment according to the first embodiment;

FIG. 26 is a view exemplarily showing a method of calculating the display position of an indicator in FIG. 25;

DETAILED DESCRIPTION

In general, according to one embodiment, a medical information display apparatus includes processing circuitry. The processing circuitry displays first medical information over a first period along a first time axis and second medical information over a second period along a second time axis, acquires time information at a time point or in a range designated in the first period about the first medical information displayed, decides a position on the second time axis which corresponds to the time information, and displays an indicator indicating the position in an area displaying the second medical information.

An embodiment of a medical information display apparatus will be described below with reference to the accompanying drawings.

Figure 1:
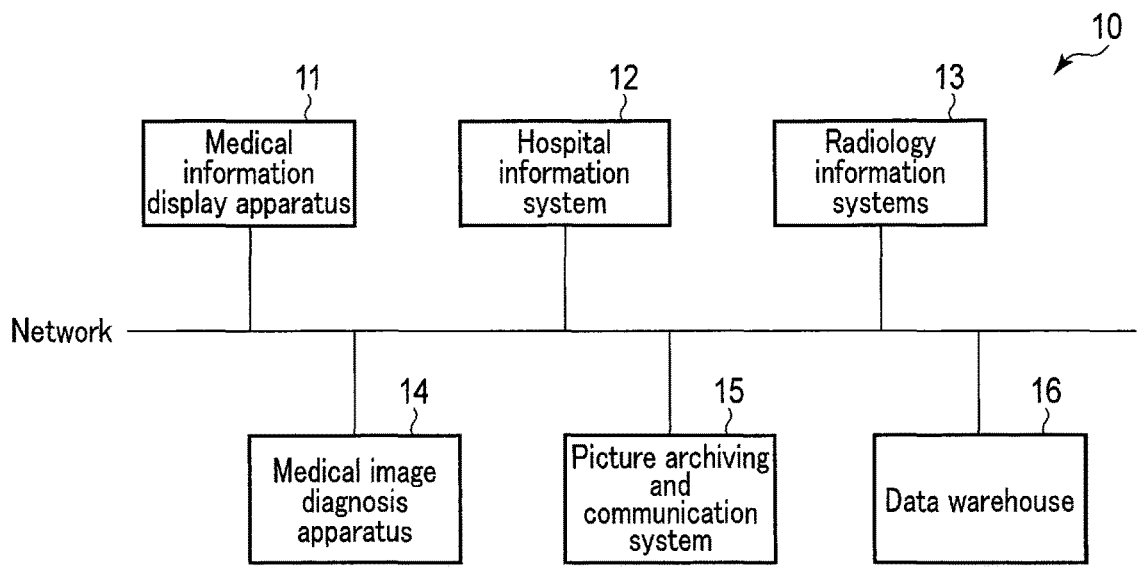
FIG. 1 is a block diagram showing the arrangement of a medical treatment information system including a medical information display apparatus according to an embodiment.

FIG. 1 shows an example of the arrangement of a medical information system including the medical information display apparatus according to an embodiment. As shown in FIG. 1, a medical information system 10 includes a medical information display apparatus 11, an HIS (Hospital Information Systems) 12, a RIS (Radiology Information Systems) 13, a medical image diagnosis apparatus 14, a PACS (Picture Archiving and Communication Systems) 15, and a DWH (Data WareHouse) 16. The medical information system 10, the medical information display apparatus 11, the HIS 12, the RIS 13, the medical image diagnosis apparatus 14, the PACS 15, and the DWH 16 are communicably connected to each other via a network (intra-hospital network) such as a LAN (Local Area Network).

The medical information display apparatus 11 is, for example, an apparatus that enables integrated observation of medical treatment information. The medical information display apparatus 11 implements, for example, an integrated viewer. The integrated viewer is an application for integrally presenting medical treatment information to the user. The medical treatment screen displayed on the integrated viewer is, for example, a screen to be displayed to allow an operator such as a medical treatment doctor to integrally observe medical treatment information about a specific patient so as to perform diagnosis and medical treatment for the patient. The integrated viewer may use any of the following implementation forms such as a Web application, a fat client application, and a thin client application. Assume that in the following description, "a medical treatment screen" is "a medical treatment screen displayed on the integrated viewer". Note that the specific arrangement of the medical information display apparatus 11 will be described later.

The HIS 12 includes, for example, an electronic health record system that manages information concerning electronic health records. Information concerning an electronic health record includes, for example, patient information and medical treatment information.

Patient information is information unique to a patient, and includes, for example, a patient ID, patient name, sex, date of birth, and age. Medical treatment information is information that can be known by a medical worker, such as the physical status of a patient, a medical condition, and medical treatment, in the process of medical treatment. Medical treatment information includes, for example, image information, examination history information, electrocardiogram information, vital sign information, medication history information, report information, medical record description information, and nursing record information.

Image information is information representing the location of a medical image obtained by imaging a patient. Image information includes, for example, information representing the location of a medical image file (to be described later) generated by the medical image diagnosis apparatus 14 that has executed an examination.

Examination history information is information representing, for example, the history of examination results obtained by performing specimen examination, bacteria examination, and the like with respect to a patient.

Electrocardiogram information is information concerning the electrocardiographic waveform measured from a patient.

Vital sign information is basic information concerning the life of a patient. Vital sign information includes, for example, a pulse rate, respiration rate, oxygen concentration, body temperature, blood pressure, and level of consciousness. Medication history information is information representing, for example, the history of the amounts of medicines administered to a patient.

Report information is information obtained by a reading doctor in a radiology department by diagnostically reading medical images such as X-ray images, CT images, MRI images, and ultrasonic images in response to an examination request from a medical treatment doctor in a diagnosis and treatment department and summarizing information about the condition and disease of the patient. Report information includes, for example, reading report information representing the reading report generated by a reading doctor by referring to a medical image file stored in the PACS 15. Note that report information is generally stored in the PACS 15, and hence the electronic health record system can display report information by reading out the report information from the PACS 15.

Medical record description information is, for example, information input to an electronic health record by a medical treatment doctor or the like. Medical record description information includes, for example, a medical treatment record at hospital admission, the medical history of a patient, and a medication prescription history.

Nursing record information is, for example, information input to an electronic health record by a nurse or the like. Nursing record information includes a nursing record at hospital admission.

Information concerning an electronic health record includes, for example, examination execution information. Examination execution information is generated by the medical image diagnosis apparatus 14, which has executed an examination according to examination order information. Examination execution information is information representing the examination executed by the medical image diagnosis apparatus 14. Examination execution information includes an order number, examination UID (Unique ID), patient ID, modality type, imaging region, and imaging conditions.

An examination UID is an identifier that can uniquely specify an examination. A modality type represents the modality used for imaging. Modality types include, for example, "X-ray computed tomography apparatus", "X-ray diagnosis apparatus", "magnetic resonance imaging apparatus", and "ultrasonic diagnosis apparatus". An imaging region corresponds to an examination region included in examination order information. Imaging regions include, for example, an abdomen, brain, and breast. Imaging conditions include a body posture, imaging direction, and whether to use a contrast medium.

The HIS 12 includes an order system that manages reservation information, order information, and the like. Note that the HIS 12 is configured to include an electronic health record system and an ordering system.

Reservation information includes, for example, information concerning a clinical consultation reservation, examination reservation, and the like. Information concerning a clinical consultation reservation includes, for example, a clinical consultation day, clinical consultation time, receipt number, doctor for clinical consultation, and department for clinical consultation. Information concerning an examination reservation includes, for example, an examination day, examination time, and receipt number.

Order information is, for example, information concerning an order requested by a clinical consultation doctor or the like, and is, for example, order information concerning an image examination, specimen examination, physiological examination, prescription, and medicine administration.

When order information is examination order information for requesting an image examination, the examination order information includes, for example, an order number that can identify an examination, patient ID, examination type, examination region, and request source information. An order number is a number issued when examination order information is input, and is, for example, an identifier for uniquely specifying examination order information in one hospital. Examination types include an X-ray examination, CT (computed Tomography) examination, MR (Magnetic Resonance) examination, and RI (Radio Isotope) examination. Examination regions include, for example, an abdomen, brain, and breast. Request source information includes a clinical consultation department name and the name of a doctor in charge. Information concerning an examination reservation is linked to order information.

The RIS 13 is a system that manages examination reservation information associated with a radiographic examination service. For example, the RIS 13 collects examination order information input from clinical consultation doctors in an order system included in the HIS 12 upon adding various types of setting information to the examination order information, and manages the collected information as examination reservation information. Note that the RIS 13 may add various types of setting information to examination order information by using radiation records recording various types of setting information set in the medical image diagnosis apparatus 14 in past examinations. The RIS 13 transmits an examination order to the medical image diagnosis apparatus 14 according to examination reservation information. The RIS 13 also transmits the examination execution information generated by the medical image diagnosis apparatus 14 used to execute an examination to an electronic health record system included in the HIS 12.

The medical image diagnosis apparatus 14 is an apparatus that executes an examination by, for example, imaging a patient. The medical image diagnosis apparatus 14 includes, for example, an X-ray computed tomography apparatus, X-ray diagnosis apparatus, magnetic resonance imaging apparatus, nuclear medicine diagnosis apparatus, and ultrasonic diagnosis apparatus. The medical image diagnosis apparatus 14 executes an examination based on, for example, the examination reservation information transmitted from the RIS 13. The medical image diagnosis apparatus 14 generates examination execution information and transmits it to the RIS 13.

The medical image diagnosis apparatus 14 generates medical image data by executing an examination. Medical image data is, for example, X-ray CT image data, X-ray image data, MRI image data, nuclear medicine image data, or ultrasonic image data. The medical image diagnosis apparatus 14 generates a medical image file by converting generated medical image data into a form complying with the DICOM (Digital Imaging and Communication in Medicine) standards. A medical image file is, for example, a file in a form complying with the DICOM standards. The medical image diagnosis apparatus 14 transmits the generated medical image file to the PACS 15.

The PACS 15 is a system that manages various types of medical image files. The PACS 15 stores, for example, the medical image file transmitted from the medical image diagnosis apparatus 14. Note that the PACS 15 may store report information attached to a medical image file or report information about examinations associated with a plurality of medical image files.

The DWH 16 is a database system that collectively accumulates, for example, information generated by healthcare providers, that is, medical treatment big data. The DWH 16 is implemented by, for example, a general server apparatus. The DWH 16 includes, for example, processing circuitry, a memory, and a communication interface. The processing circuitry, memory, and communication interface are communicably connected to each other via, for example, a bus.

Figure 2:
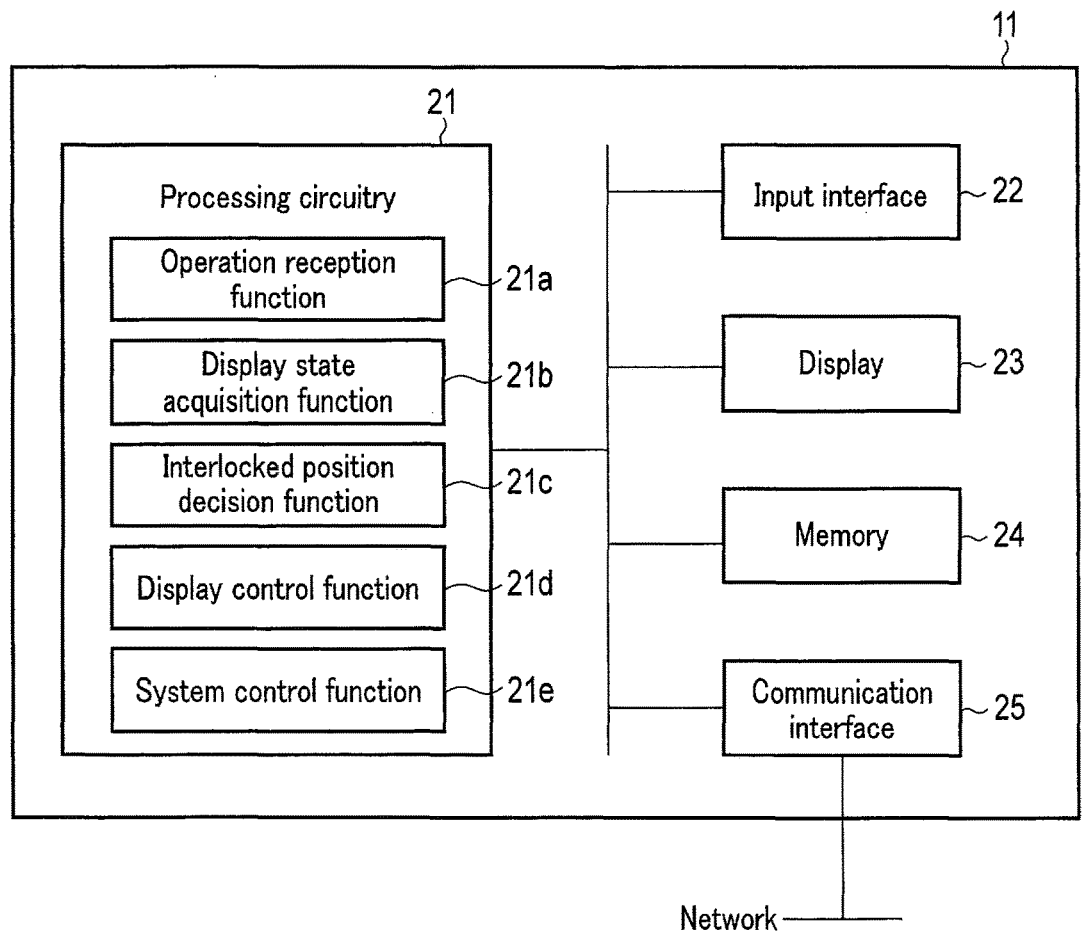
FIG. 2 is a block diagram showing an example of the arrangement of the medical information display apparatus in FIG. 1.

FIG. 2 shows an example of the arrangement of the medical information display apparatus in FIG. 1. As shown in FIG. 2, the medical information display apparatus 11 includes processing circuitry 21, an input interface 22, a display 23, a memory 24, and a communication interface 25. The processing circuitry 21, the input interface 22, the display 23, the memory 24, and the communication interface 25 are communicably connected to each other via, for example, a bus.

The processing circuitry 21 includes a processor and memories such as a ROM (Read-Only Memory) and RAM (which are not shown) as hardware resources, and controls the medical information display apparatus 11. The processing circuitry 21 includes an operation reception function 21a, a display state acquisition function 21b, an interlocked position decision function 21c, a display control function 21d, and a system control function 21e. The various types of functions implemented by the operation reception function 21a, the display state acquisition function 21b, the interlocked position decision function 21c, the display control function 21d, and the system control function 21e of the processing circuitry 21 are stored in a memory in the form of programs that can be executed by a computer. The processing circuitry 21 is a processor that reads out and executes programs corresponding to various types of functions to implement functions corresponding to the respective programs. In other words, the processing circuitry 21 that has read out programs obtains a plurality of functions indicated by the processing circuitry 21 in FIG. 2.

Although according to the above description made with reference to FIG. 2, the single processing circuitry 21 implements the various types of functions described above, a plurality of independent processors may implement the various types of functions by executing programs. In other words, one processing circuitry may execute each of the various types of programs described above configured as programs, or specific functions may be implemented in dedicated independent program execution circuits.

The term "processor" used in the above description means, for example, a CPU (Central Processing Unit), a GPU (Graphics Processing Unit), or circuitry such as an ASIC (Application Specific Integrated Circuit), or a programmable logic device (for example, SPLD (Simple Programmable Logic Device), CPLD (Complex Programmable Logic Device), or FPGA (Field Programmable Logic Device)).

The processor in the processing circuitry 21 implements various types of functions by reading out and executing programs saved in the memory 24. Note that programs may be directly incorporated in circuitry in the processor instead of saving the programs in the memory 24. In this case, the processor implements functions by reading out and executing programs incorporated in the circuitry in the processor.

The processing circuitry 21 causes the operation reception function 21a to receive an operation by the operator via the input interface 22 on the medical treatment screen displayed on the integrated viewer. A medical treatment screen includes, for example, an area indicating a timeline (to be referred to as a timeline area hereinafter) and an area indicating medical treatment information (to be referred to as a medical treatment information area hereinafter).

The timeline area is, for example, an area displaying a plurality of pieces of medical treatment information about a specific patient in time series in date and time order. Medical treatment information includes, for example, information about "specimen examination" corresponding to examination history information of an electronic health record, information about "image examination" corresponding to image information of the electronic health record, and information about "medical record description", and information about "nursing record". In addition, the timeline area may display information about "event" indicating hospital admission and discharge dates and times of a specific patient, operation date and time, and the like.

The above individual medical treatment information is arranged in a timeline area in the form of an individual icon. A medical treatment area includes, for example, one or more areas capable of displaying individual medical treatment information. More specifically, the medical treatment information area can display, for example, one or more pieces of image information in an image examination, vital sign information, specimen examination information, information about a medical treatment record including a medical record description and nursing record. For example, a rectangular medical treatment information area can display image information in an image examination in the left half area, vital sign information in the upper area of the right half, and medical treatment record information in the lower area of the right half.

In other words, the medical treatment screen includes a timeline area (for example, a first area) displaying medical treatment information (for example, first medical information) on a timeline over a first period and a medical treatment information area (for example, a second area) displaying medical treatment information (for example, second medical information) over a second period.

Alternatively, the medical treatment screen displays first medical information over a first period along a first time axis and second medical information over a second period along a second time axis. A time axis indicates, for example, that data are arranged in time series in the horizontal or vertical direction. A period indicates, for example, a period of data, of data arranged along a time axis, which is actually displayed on the display.

Note that the first period may be longer than the second period and contain the second period. Alternatively, the second period may be longer than the first period and contain the first period.

Figure 3:
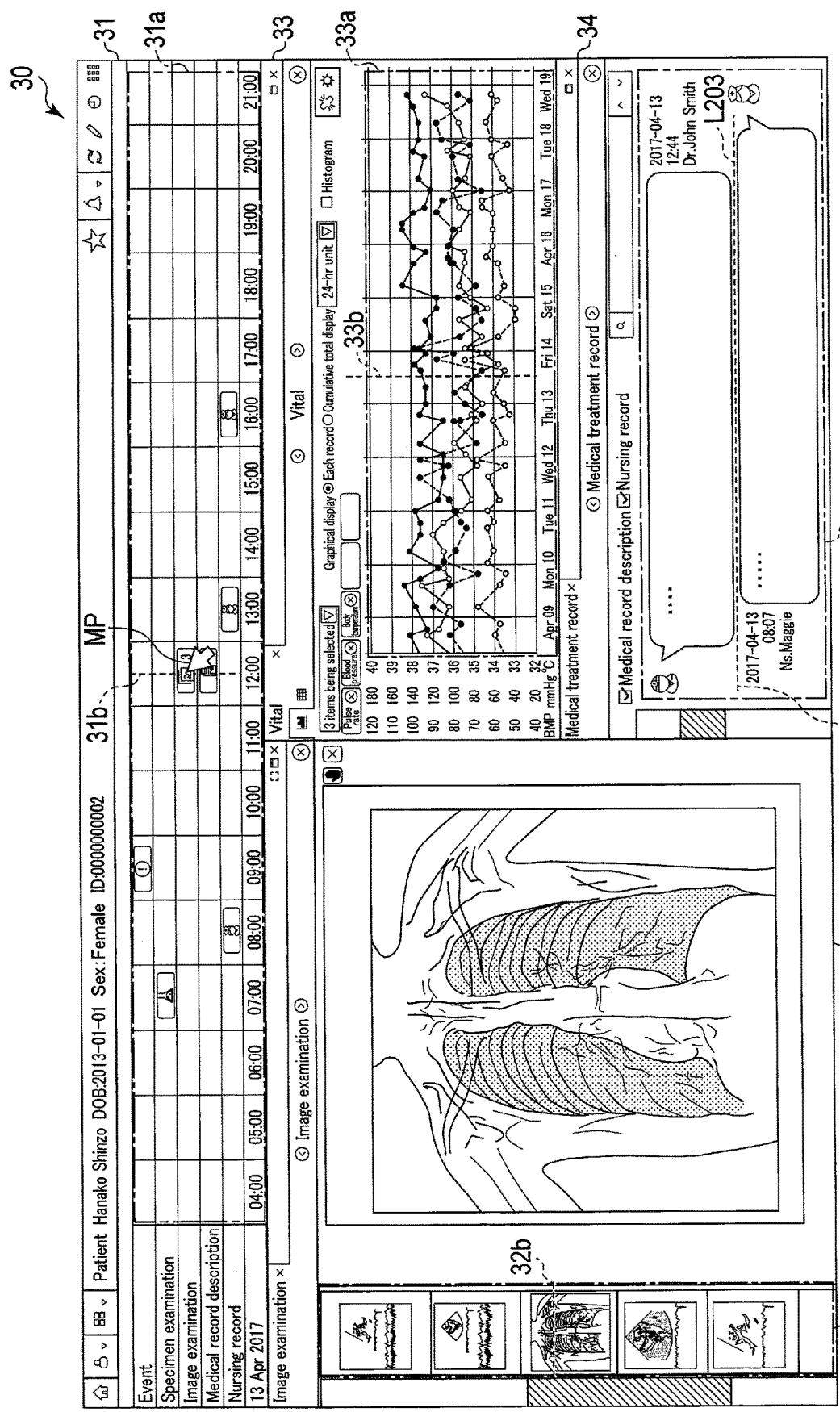
FIG. 3 is a view showing an example of the arrangement of a medical treatment screen displayed on a display in FIG. 2.

FIG. 3 is a view showing an example of the arrangement of the medical treatment screen displayed on the display in FIG. 2. As shown in FIG. 3, a medical treatment screen 30 includes a timeline area 31 and medical treatment information area divided into an image information area 32 that displays an image for an image examination, a vital sign information area 33 that displays vital sign information, and a medical treatment record information area 34 that displays the information of a medical treatment record.

The timeline area 31 includes an information display area 31a that displays a plurality of icons respectively corresponding to a plurality of pieces of medical treatment information over the period from "04:00" to "21:00" on "Apr. 13, 2017".

The information display area 31a includes an indicator 31b indicating the position of the date and time designated by the operator (designated date and time "12:00 on Apr. 13, 2017"). The operator designates a date and time by, for example, causing the display to display the indicator 31b by moving a mouse pointer MP via a mouse and clicking an arbitrary position in the information display area 31a. Alternatively, the operator may designate a date and time by causing the display to display the indicator 31b by selecting an arbitrary icon displayed in the information display area 31a. When the operator has selected an arbitrary icon, the designated date and time are the date and time linked to medical treatment information corresponding to the arbitrary icon. Note that the operator may designate a date and time by inputting the date and time to a dialog box. The time axis of the information display area 31a is in the horizontal direction.

The operator may designate a plurality of dates and times. When the operator has designated a plurality of dates and times, a plurality of indicators are displayed in the information display area 31a. These indicators may respectively have different forms. For example, the indicators may have different line types or colors.

The operator may also designate a day, month, and year and the like in addition to a date and time. These dates and times, days, months, and years, and the like may also be called time information. In addition, time information may be information within the range of dates and times. For example, time information may be information within the range of two dates associated with two data or the range of two dates designated regardless of data.

The image information area 32 includes an information display area 32a that displays thumbnails of examination images concerning a specific patient over a certain period in a time-series order (for example, in descending order of dates and times of images from the top of the screen). That is, the time axis of the information display area 32a is in the vertical direction. The information display area 32a includes an indicator 32b indicating a position corresponding to a designated date and time. Subsequently, "a thumbnail of an examination image" will be simply referred to as "a thumbnail". Note that a position corresponding to a designated date and time in the information display area 32a corresponds to, for example, the upper or lower portion of a thumbnail attached with the date and time closest to the designated date and time. This position may be located above a thumbnail.

The vital sign information area 33 includes an information display area 33a that displays vital sign information about a specific patient over the period from "Apr. 9, 2017 to Apr. 19, 2017". The information display area 33a includes an indicator 33b indicating a position corresponding to a designated date and time. The time axis of the information display area 33a is in the horizontal direction.

The medical treatment record information area 34 includes an information display area 34a that displays the comments made by a doctor and a nurse concerning a specific patient over a certain period in a time-series order (for example, in descending order of dates and times of comments from the top of the screen). That is, the time axis of the information display area 34a is in the vertical direction. The information display area 34a includes an indicator 34b indicating a position corresponding to a designated date and time. Note that a position corresponding to a designated date and time in the medical treatment record information area corresponds to, for example, the upper or lower portion of a comment associated with the date and time closest to the designated date and time. This position may be located above a comment.

In summary, according to the embodiment, the indicator 32b, the indicator 33b, and the indicator 34b are automatically set (or displayed) in response to setting the indicator 31b first on the medical treatment screen 30.

According to the above description, a date and time are designated in the information display area 31a. However, this is not exhaustive. A date and time can be designated in any of the information display area 32a, the information display area 33a, and the information display area 34a. For example, the embodiment may be configured to automatically set the indicator 31b, the indicator 32b, and the indicator 34b in response to setting the indicator 33b first on the medical treatment screen 30.

The processing circuitry 21 causes the display state acquisition function 21b to acquire various types of information concerning the medical treatment screen displayed on the integrated viewer. For example, the processing circuitry 21 acquires time information concerning a time point or range designated in a first period with respect to first medical information displayed. More specifically, the processing circuitry 21 causes the display state acquisition function 21b to acquire a period of medical treatment information displayed in the timeline area, a period of medical treatment information displayed in one or more areas in the medical treatment information area, and a date and time designated in an area (for example, the first area) selected by the operator.

The processing circuitry 21 may cause the display state acquisition function 21b to acquire an operation instruction (first instruction) to cancel the selection of a designated date and time.

The processing circuitry 21 causes the interlocked position decision function 21c to decide a position, in an area (for example, a second area) different from an arbitrary area (for example, a first area) on the medical treatment screen, which is interlocked with a date and time designated in the arbitrary area. For example, the processing circuitry 21 decides a position on the second time axis which corresponds to acquired time information. More specifically, the processing circuitry 21 causes the interlocked position decision function 21c to decide a position concerning the date and time designated in the second area based on the date and time designated in the first area and a period of medical treatment information (for example, a second period) displayed in the second area different from the first area.

More specifically, the processing circuitry 21 causes the interlocked position decision function 21c to decide a position concerning a designated date and time based on whether the designated date and time are included in the second period. If the designated date and time are included in the second period, the processing circuitry 21 decides a position corresponding to the designated date and time. If the designated date and time are not included in the second period, the processing circuitry 21 decides a position corresponding to the date and time closest to the designated date and time in the second period.

The processing circuitry 21 causes the display control function 21d to make the display 23 display a medical treatment screen. The medical treatment screen includes first medical information over a first period along the first time axis and second medical information over a second period along the second time axis. Alternatively, the medical treatment screen includes at least a first area displaying first medical information over a first period and a second area displaying second medical information over a second period. The processing circuitry 21 further causes the display control function 21d to display an indicator indicating a decided position in the second area displaying second medical information. Note that the information of the decided position may be included in the second medical information or may be included as an indicator in the second area. That is, it is only required to allow the operator to visually check a decided position in any of the areas on the medical treatment screen.

The processing circuitry 21 may also cause the display control function 21d to display second medical information having a navigation area including an indicator indicating a decided position in a second area. The processing circuitry 21 may cause the display control function 21d to display medical information corresponding to designated time information as a preview in the second area. Alternatively, the processing circuitry 21 may cause the display control function 21d to display second medical information having a preview area including information concerning designated time information, which is not included in the second period, in the second area.

The processing circuitry 21 may also cause display control function 21d to make the display 23 display the first area and the second area which are positioned such that decided positions are located in the centers of the display areas. In other words, the processing circuitry 21 may display a position on the first time axis and a position on the second time axis, which correspond to designated time information, so as to make the respective positions coincide with the center of the first area and the center of the second area.

The processing circuitry 21 may also cause the display control function 21d to make the display 23 switchably display the display state of each of the first and second areas before positioning and the display state of each of the first and second areas after positioning.

The processing circuitry 21 may cause the display control function 21d to make the display 23 display the second area from which a decided position is removed in accordance with a selection cancel instruction. In other words, the processing circuitry 21 may display the second area from which an indicator indicating a decided position is removed in accordance with a selection cancel instruction.

The processing circuitry 21 causes the system control function 21e to control the basic operations of the medical information display apparatus 11, such as an input/output operation and a communication operation. Upon executing the system control function 21e, the processing circuitry 21 receives various types of requests via the input interface 22. The processing circuitry 21 executes various types of functions in accordance with various types of received requests.

The operation reception function 21a, the display state acquisition function 21b, the interlocked position decision function 21c, the display control function 21d, and the system control function 21e may be incorporated as control programs in the processing circuitry 21 or dedicated hardware circuits that can execute the respective functions may be incorporated in the processing circuitry 21 itself.

The input interface 22 is implemented by, for example, a mouse, a keyboard, and a touch panel having an operation screen which the operator touches to input an instruction. The input interface 22 accepts, for example, operations from the operator. The operations of the operator correspond to, for example, a mouse pointer moving operation, clicking operation, drag-and-drop operation, and the like. The input interface 22 converts an operation from the operator into an electrical signal and outputs the electrical signal to the processing circuitry 21.

The display 23 displays various types of information for the execution of various types of services by the operator. The display 23 displays a medical treatment screen under the control of the processing circuitry 21. As the display 23, for example, a CRT display, liquid crystal display, organic EL display, LED display, plasma display, or another arbitrary display known in the art can be used, as appropriate.

The memory 24 stores various types of information. As the memory 24, for example, an HDD (Hard Disk Drive), SSD (Solid State Drive), integrated circuit storage device, or the like can be used, as appropriate. In addition, the memory 24 may be a driving device or the like that reads and writes various types of information between portable storage media such as a CD-ROM drive, DVD drive, and flash memory.

The communication interface 25 performs data communication with the HIS 12, the RIS 13, the medical image diagnosis apparatus 14, the PACS 15, and the DWH 16 that are connected to each other via an intra-hospital network. Any communication standards can be used for the HIS 12, the RIS 13, the medical image diagnosis apparatus 14, the PACS 15, and the DWH 16. For example, either or both of HL7 and DICOM can be used.

Figure 4:
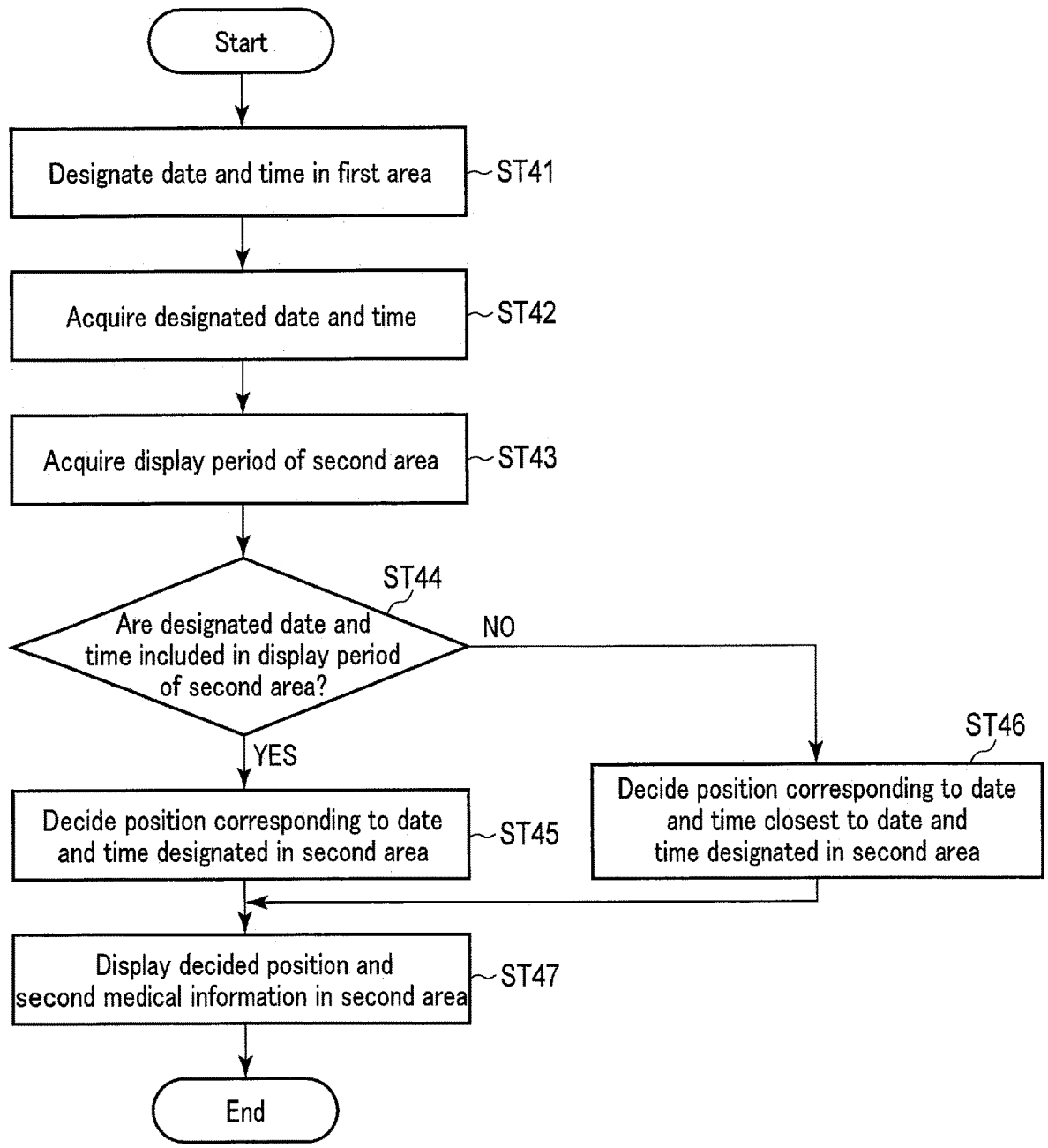
FIG. 4 is a flowchart exemplarily showing processing executed by processing circuitry in FIG. 2.

FIG. 4 is a flowchart exemplarily showing processing executed by the processing circuitry in FIG. 2. The processing circuitry 21 starts the processing in FIG. 4 by executing a program associated with interlocking display of a designated date and time in response to the execution of the integrated viewer by the operator or the like.

The following description will be made with reference to the medical treatment screen 30 in FIG. 3 on the assumption that the first area is a timeline area, and the second area is a vital information area. However, this is not exhaustive. For example, the first area may be the vital information area, and the second area may be the timeline area. In addition, both the first area and the second area may display the same information. That is, it is only required that the date and time designated in the first area are displayed at a position associated with the date and time in the second area in an interlocking manner.

(Step ST41)

The processing circuitry 21 causes the operation reception function 21a to receive the operation of designating a date and time in the first area by the operator. This operation corresponds to the operation of displaying the indicator 31b by the designation of a date and time by the operator with the mouse pointer MP.

(Step ST42)

The processing circuitry 21 causes the display state acquisition function 21b to acquire the date and time designated in the first area. The first area is, for example, the information display area 31a. The designated date and time are, for example, date and time "12:00 on Apr. 13, 2017" corresponding to the position of the indicator 31b. In other words, the processing circuitry 21 acquires designated date and time "12:00 on Apr. 13, 2017" in the information display area 31a.

(Step ST43)

The processing circuitry 21 causes the display state acquisition function 21b to acquire the display period of medical treatment information in the second area different from the first area. The second area is, for example, the information display area 33a in the vital sign information area 33. The display period in the second area corresponds, for example, display period "from Apr. 9, 2017 to Apr. 19, 2017" in the information display area 33a. In other words, the processing circuitry 21 acquires display period "from Apr. 9, 2017 to Apr. 19, 2017" in the information display area 33a.

(Step ST44)

The processing circuitry 21 causes the interlocked position decision function 21c to determine whether the designated date and time are included in the display period in the second area. If the designated date and time are included in the display period in the second area (YES in step ST44), the process advances to step ST45. Otherwise (NO in step ST44), the process advances to step ST46.

According to the medical treatment screen 30, because designated date and time "12:00 on Apr. 13, 2017" are included in display period "from Apr. 9, 2017 to Apr. 19, 2017", the process advances to step ST45.

Figure 5:
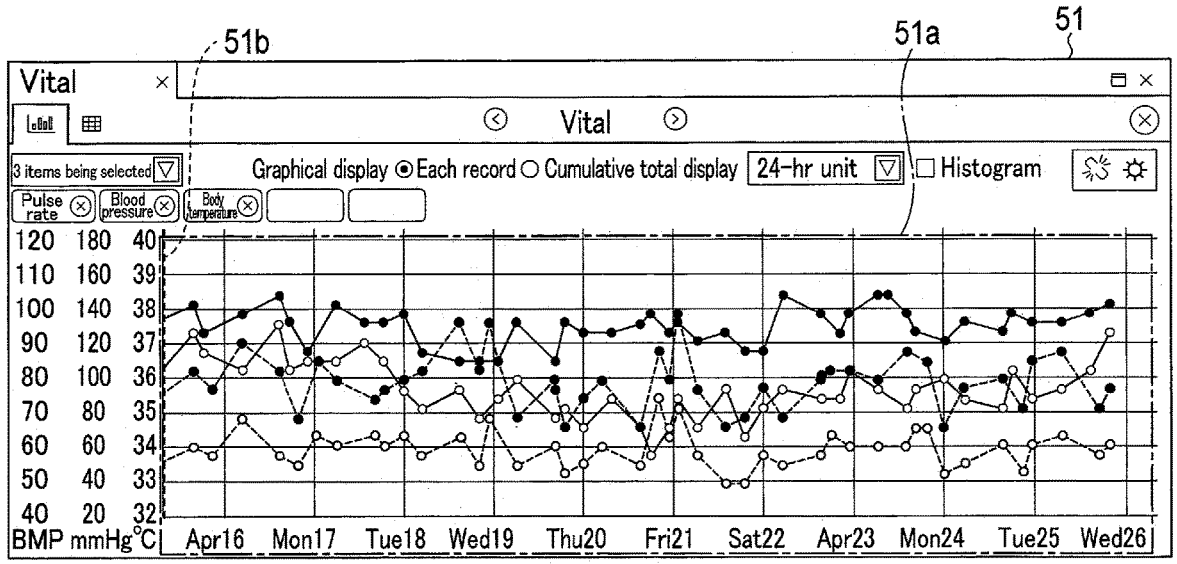
FIG. 5 is a view showing another display example of a vital sign information area in FIG. 3.

FIG. 5 is a view showing another display example of the vital sign information area in FIG. 3. As shown in FIG. 5, a vital sign information area 51 includes an information display area 51a displaying vital sign information concerning a specific patient over the period "from Apr. 16, 2017 to Apr. 26, 2017". The information display area 51a includes an indicator 51b indicating a position corresponding to the date and time ("12:00 on Apr. 15, 2017") closest to the designated date and time (for example, "12:00 on Apr. 13, 2017").

Assume that the vital sign information area 33 on the medical treatment screen 30 is in the vital sign information area 51. In this case, the processing circuitry 21 acquires display period "from Apr. 16, 2017 to Apr. 26, 2017" in the information display area 51a in step ST43. That is, according to the medical treatment screen 30 displaying the vital sign information area 51, because designated date and time "12:00 on Apr. 13, 2017" are not included in display period "from Apr. 16, 2017 to Apr. 26, 2017", the process advances to step ST46.

(Step ST45)

The processing circuitry 21 causes the interlocked position decision function 21c to decide a position corresponding to the designated date and time in the second area. The position corresponding to the designated date and time corresponds to, for example, the position of the indicator 33b. After step ST45, the process advances to step ST47.

(Step ST46)

The processing circuitry 21 causes the interlocked position decision function 21c to decide a position corresponding to the date and time closest to the designated date and time in the second area. The position corresponding to the date and time closest to the designated date and time corresponds to, for example, the position of the indicator 51b. After step ST46, the process advances to step ST47.

(Step ST47)

The processing circuitry 21 causes the display control function 21d to display the decided position and the second medical information in the second area. More specifically, the processing circuitry 21 displays the indicator 33b on the vital sign information area 33 or displays the indicator 51b on the vital sign information area 51. After step ST47, the processing is terminated.

Figure 6:
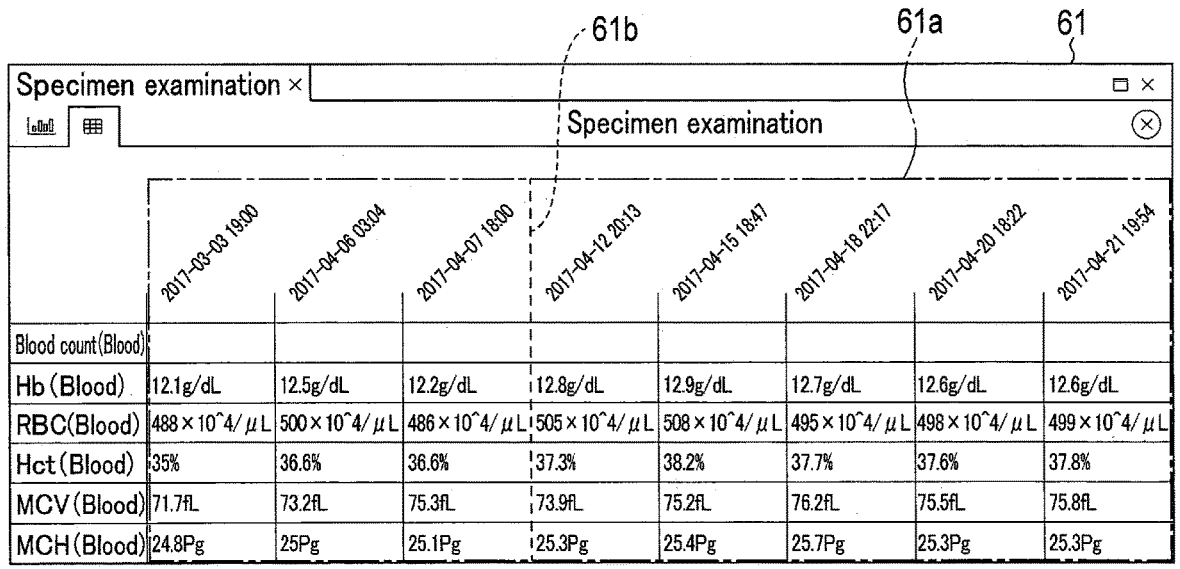
FIG. 6 is a view showing a display example of a specimen examination information area according to the embodiment.

FIG. 6 is a view showing a display example of a specimen examination information area according to the embodiment. FIG. 6 shows a specimen examination information area 61 that displays specimen examination information. The specimen examination information area 61 includes an information display area 61a that displays specimen examination information concerning a specific patient over a certain period in a time-series order (for example, in descending order of dates and times of examination results from the right of the screen). A certain period in the specimen examination information area 61 corresponds to, for example, the period from the date and time of the oldest examination result displayed to the date and time of the newest examination result displayed.

The information display area 61a includes, for example, an indicator 61b indicating a position corresponding to designated date and time "12:00 on Apr. 10, 2017". The indicator 61b is displayed between the examination result at "18:00 on Apr. 7, 2017" and the examination result at "20:13 on Apr. 12, 2017".

Figures 7, 8:
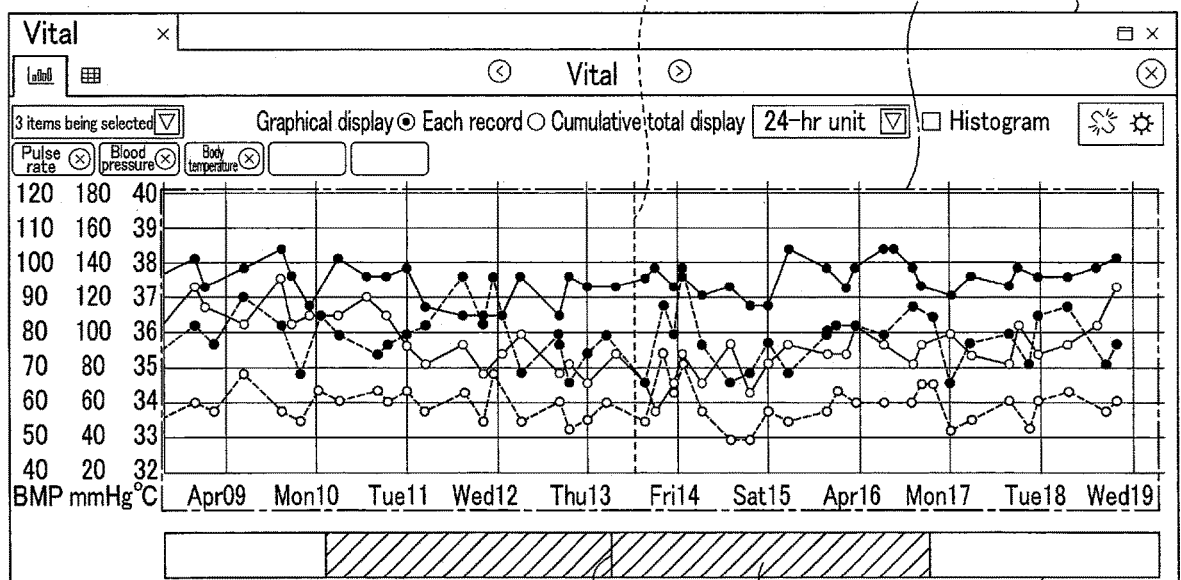
FIG. 7 is a view showing another display example of the specimen examination information area according to the embodiment.
FIG. 8 is a view showing a display example of a vital sign information area including a navigation area according to the embodiment.

FIG. 7 is a view showing another display example of the specimen examination information area according to the embodiment. As shown in FIG. 7, a specimen examination information area 71 includes an information display area 71a. The information display area 71a includes an indicator 71b indicating the position of the date and time closest to designated date and time "12:00 on Apr. 29, 2017". The indicator 71b is displayed, for example, on the right side of the examination result at "19:54 on Apr. 21, 2017" closest to designated date and time "12:00 on Apr. 29, 2017".

FIG. 8 is a view showing a display example of a vital sign information area including a navigation area according to the embodiment. As shown in FIG. 8, a vital sign information area 81 includes an information display area 81a and a navigation area 82a.

The information display area 81a displays vital sign information concerning a specific patient over the period "from Apr. 9, 2017 to Apr. 19, 2017". The information display area 81a includes an indicator 81b indicating a position corresponding to designated date and time.

The navigation area 82a includes a partial navigation area 82b corresponding to the period displayed in the information display area 81a. The partial navigation area 82b includes an indicator 82c based on the relative positional relationship between the display range of the information display area 81a and the position of the indicator 81b. More specifically, the relative positional relationship between the display range of the information display area 81a and the position of the indicator 81b corresponds to the relative positional relationship between the length of the partial navigation area 82b and the position of the indicator 82c.

FIG. 9 is a view showing an example of the arrangement of a navigation area according to the embodiment. As shown in FIG. 9, a first range 93a of a navigation area 92a indicates the existence period of data. The existence period of data is, for example, the period from the date and time when data is registered first to the date and time when data is registered last. Alternatively, the existence period of data may be the period going back from the date and time of the last registered data by a predetermined period (for example, 10 years).

A second range 93b of a partial navigation area 92b indicates the display period of the data in contrast to the existence period of the data. The display period of the data corresponds to the period of the display range of the information display area 81a in FIG. 8. Note that the partial navigation area 92b may have a scroll function of making transition of the screen of the second range 93b.

In other words, the navigation area corresponds to a period including at least the period displayed in the information display area. The partial navigation area is arranged inside the navigation area and corresponds to the period displayed in the information display area.

An indicator 92c indicates a specific position in the navigation area 92a at which the date and time designated (or decided) in the information display area are located. When, for example, the indicator 92c is displayed in the partial navigation area 92b, the indicator displayed in the information display area has a date and time included in the period displayed in the information display area.

For example, with an increase in the proportion of the partial navigation area 92b to the navigation area 92a, the amount of data displayed in the information display area increases. In contrast, with a decrease in the proportion of the partial navigation area 92b to the navigation area 92a, the amount of data displayed in the information display area decreases.

Note that the relationship between the navigation area 92a and the partial navigation area 92b may be decided based on the number of existing data. For example, when 20 data out of the total of 100 data are displayed, the partial navigation area 92b is displayed so as to occupy 20% of the navigation area 92a. Accordingly, depending on how data is displayed, the existence period of the data may be rephrased as the number of data as appropriate.

FIG. 10 shows another display example of a vital sign information area including a navigation area according to the embodiment. As shown in FIG. 10, a vital sign information area 101 includes an information display area 101a and a navigation area 102a. The information display area 101a displays vital sign information concerning a specific patient over the period "from Apr. 9, 2017 to Apr. 19, 2017".

The information display area 101a includes an indicator 101b indicating a position corresponding to the date and time closest to a designated date and time. The navigation area 102a includes a partial navigation area 102b corresponding to the period displayed in the information display area 101a. The navigation area 102a includes an indicator 102c based on the relative positional relationship between the existence period of data and a designated date and time. More specifically, the relative positional relationship between the existence period of data and a designated date and time corresponds to the relative positional relationship between the navigation area 102a and the indicator 102c.

Figure 11:
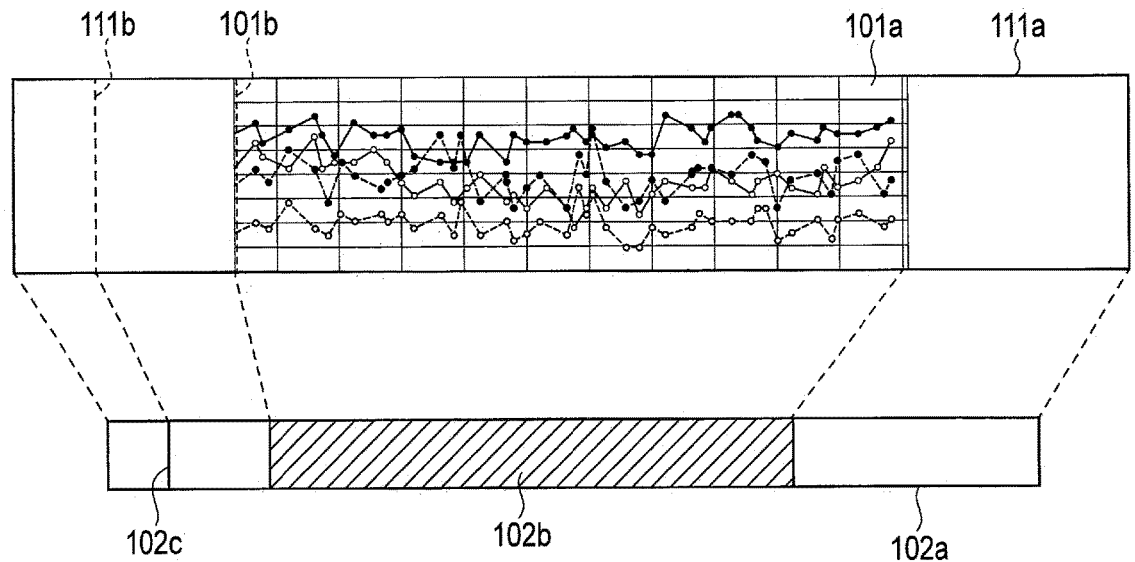
FIG. 11 is a view exemplarily showing the relationship between an information area and a navigation area according to the embodiment.

FIG. 11 exemplarily shows the relationship between an information area and a navigation area according to the embodiment. As shown in FIG. 11, a data area 111a includes the information display area 101a. Areas in the data area 111a other than the information display area 101a are areas in which data exist but are not displayed. That is, the relative positional relationship between the data area 111a and the information display area 101a corresponds to the relative positional relationship between the navigation area 102a and the partial navigation area 102b.

The indicator 102c corresponds to the position of an indicator 111b in the data area 111a. However, the position of the indicator 111b is not included in the information display area 101a, and hence is not displayed according to the prior art. According to the embodiment, however, displaying the indicator 101b at the position in the information display area 101a which is closest to the position of the indicator 111b can present an arear other than the display area to the operator.

Figure 12:
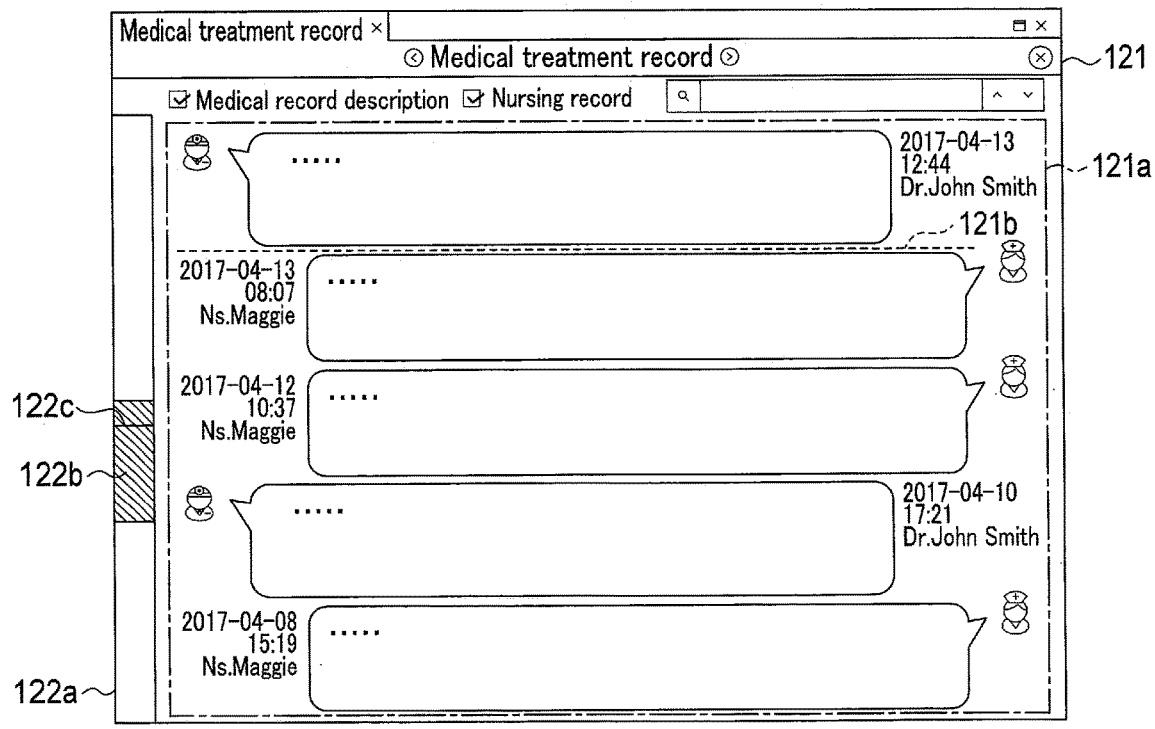
FIG. 12 is a view showing a display example of a medical treatment record information area including a navigation area according to the embodiment.

FIG. 12 shows a display example of a medical treatment record information area including a navigation area. As shown in FIG. 12, a medical treatment record information area 121 includes an information display area 121a and a navigation area 122a.

The information display area 121a displays comments made by a doctor and a nurse concerning a specific patient over a certain period. More specifically, the information display area 121a displays five comments made by the doctor and the nurse over the period from date and time "15:19 on Apr. 8, 2017" of the oldest comment displayed to date and time "12:44 on Apr. 13, 2017" of the newest comment displayed. The information display area 121*a* includes an indicator 121*b* indicating a position corresponding to a designated date and time.

The navigation area 122*a* includes a partial navigation area 122*b* corresponding to the period displayed in the information display area 121*a*. The partial navigation area 122*b* includes an indicator 122*c* based on the relative positional relationship between the display range of the information display area 121*a* and the position of the indicator 121*b*. More specifically, the relative positional relationship between the display range of the information display area 121*a* and the position of the indicator 121*b* corresponds to the relative positional relationship between the length of the partial navigation area 122*b* and the position of an indicator 122*c*.

Figure 13:
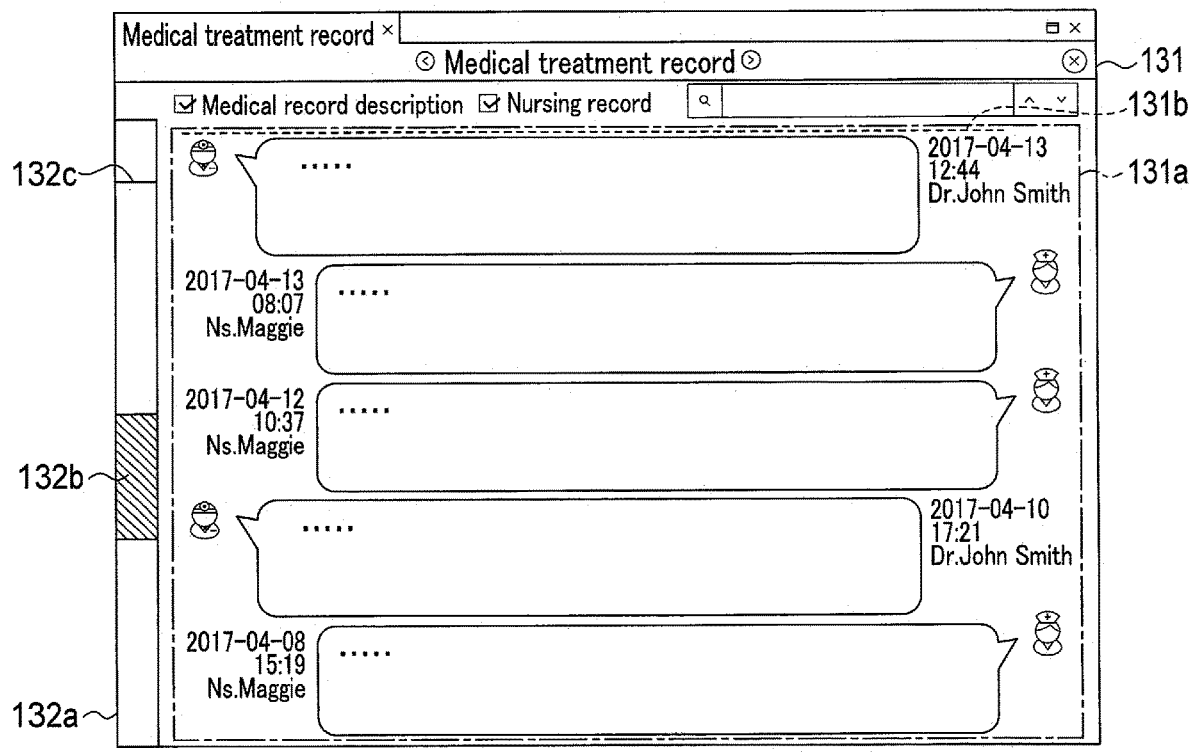
FIG. 13 is a view showing another display example of the medical treatment record information area including the navigation area according to the embodiment.

FIG. 13 shows another display example of a medical treatment record information area including a navigation area according to the embodiment. As shown in FIG. 13, a medical treatment record information area 131 includes an information display area 131*a* and a navigation area 132*a*.

The information display area 131*a* displays the comments made by the doctor and the nurse concerning the specific patient over a certain period. The comments displayed in the information display area 131*a* are the same as those in an information display area 130*a*, and hence a description of the comments will be omitted. The information display area 131*a* includes an indicator 131*b* indicating a position corresponding to the date and time closest to the designated date and time.

The navigation area 132*a* includes a partial navigation area 132*b* corresponding to the period displayed in the information display area 131*a*. The navigation area 132*a* includes an indicator 132*c* based on the relative positional relationship between the existence range of data and a designated date and time. More specifically, the relative positional relationship between the existence range of data and a designated date and time corresponds to the relative positional relationship between the navigation area 132*a* and the indicator 132*c*. Note that the existence range of data is, for example, the range in which the data of all the comments are assumed to be displayed over an existence period.

Figure 14:
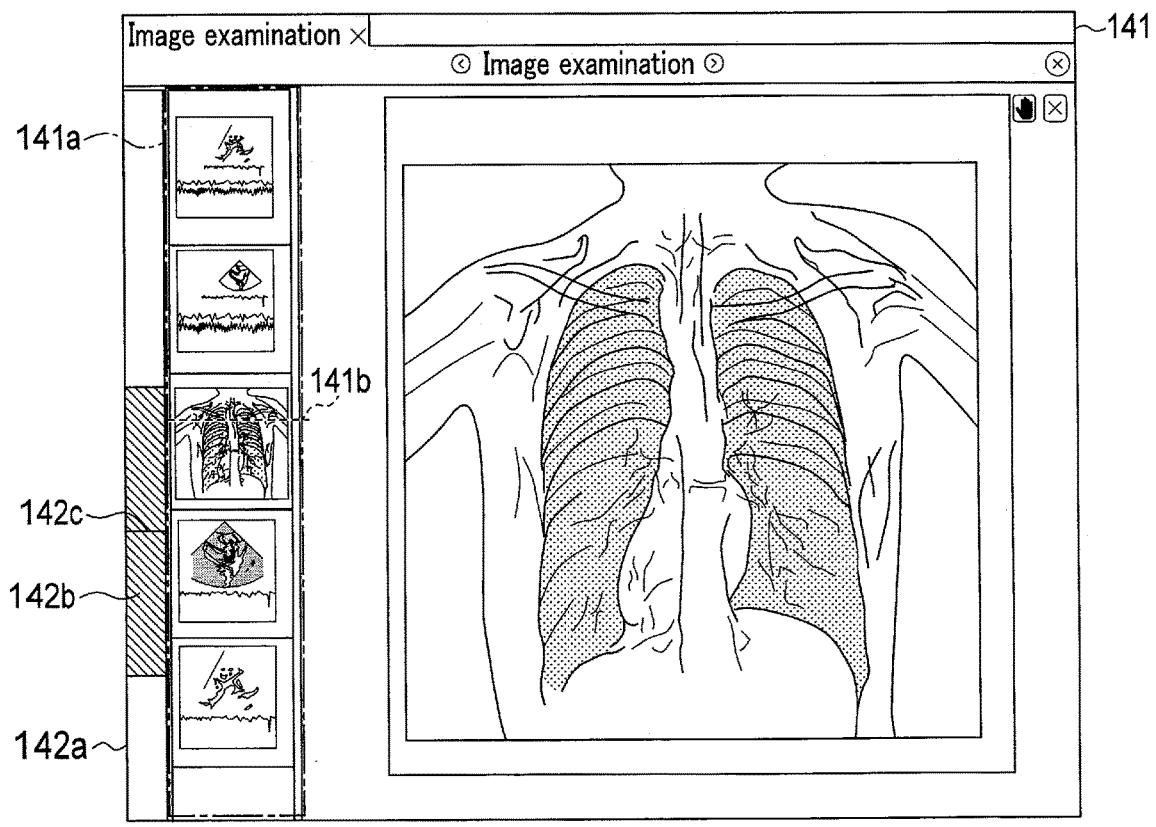
FIG. 14 is a view showing a display example of an image information area including a navigation area according to the embodiment.

FIG. 14 shows a display example of an image information area including a navigation area according to the embodiment. As shown in FIG. 14, an image information area 141 includes an information display area 141*a* and a navigation area 142*a*.

The information display area 141*a* displays thumbnails concerning a specific patient in a time-series order over a certain period. More specifically, the information display area 141*a* displays five thumbnails over the period from the date and time attached to the oldest thumbnail displayed to the date and time attached to the newest thumbnail displayed. The information display area 141*a* includes an indicator 141*b* indicating a position corresponding to the designated date and time.

A navigation area 142*a* includes a partial navigation area 142*b* corresponding to the period displayed in the information display area 141*a*. The partial navigation area 142*b* includes an indicator 142*c* based on the relative positional relationship between the display range of the information display area 141*a* and the position of the indicator 141*b*. More specifically, the relative positional relationship between the display range of the information display area 141*a* and the position of the indicator 141*b* corresponds to the relative positional relationship between the length of the partial navigation area 142*b* and the position of the indicator 142*c*.

Figure 15:
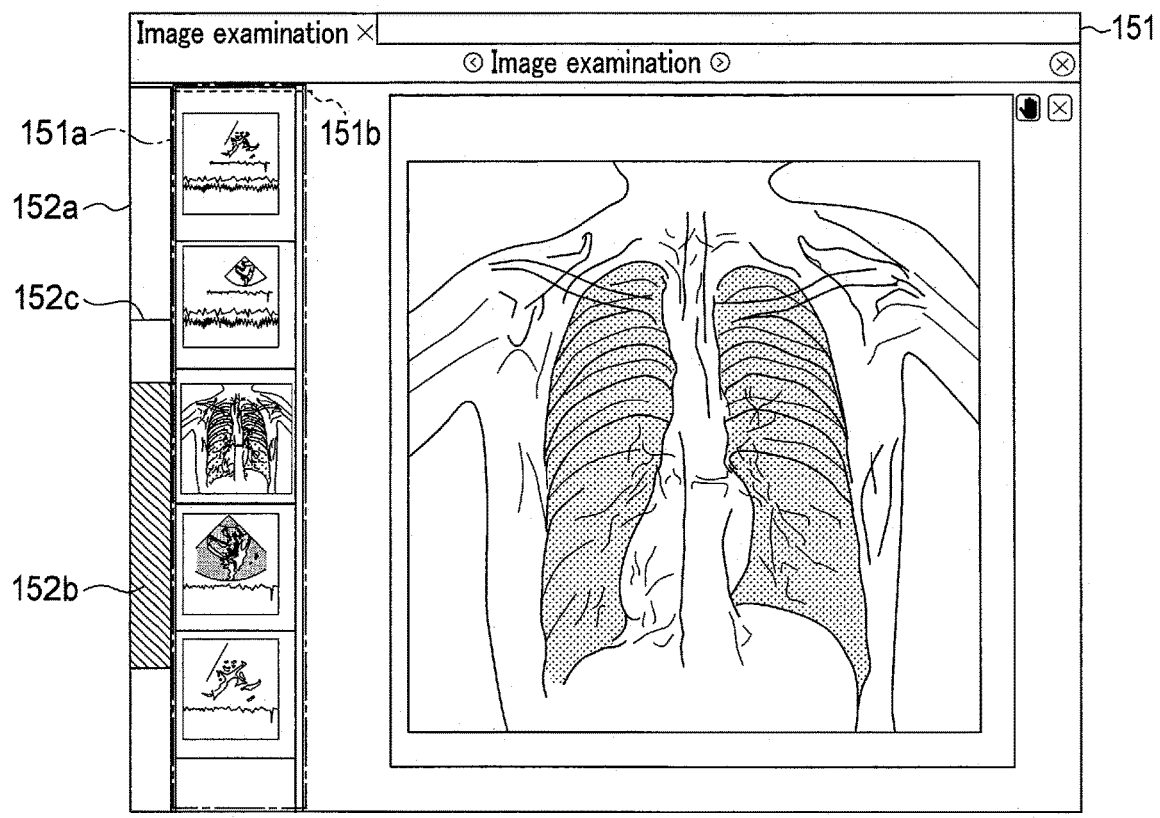
FIG. 15 is a view showing another display example of the image information area including the navigation area according to the embodiment.

FIG. 15 shows another display example of an image information area including a navigation area. As shown in FIG. 15, an image information area 151 includes an information display area 151*a* and a navigation area 152*a*.

The information display area 151*a* displays thumbnails concerning a specific patient in a time-series order over a certain period. The thumbnails displayed in the information display area 151*a* are the same as those in the information display area 141*a*, and hence a description of the thumbnails will be omitted. The information display area 151*a* includes an indicator 151*b* indicating a position corresponding to the date and time closest to the designated date and time.

The navigation area 152*a* includes a partial navigation area 152*b* corresponding to the period displayed in the information display area 151*a*. The navigation area 152*a* includes an indicator 152*c* based on the relative positional relationship between the existence range of data and the designated date and time. More specifically, the relative positional relationship between the existence range of the data and the designated date and time corresponds to the relative positional relationship between the navigation area 152*a* and the indicator 152*c*. Note that the existence range of data is, for example, the range in which all the thumbnails are assumed to be displayed over an existence period.

Figure 16:
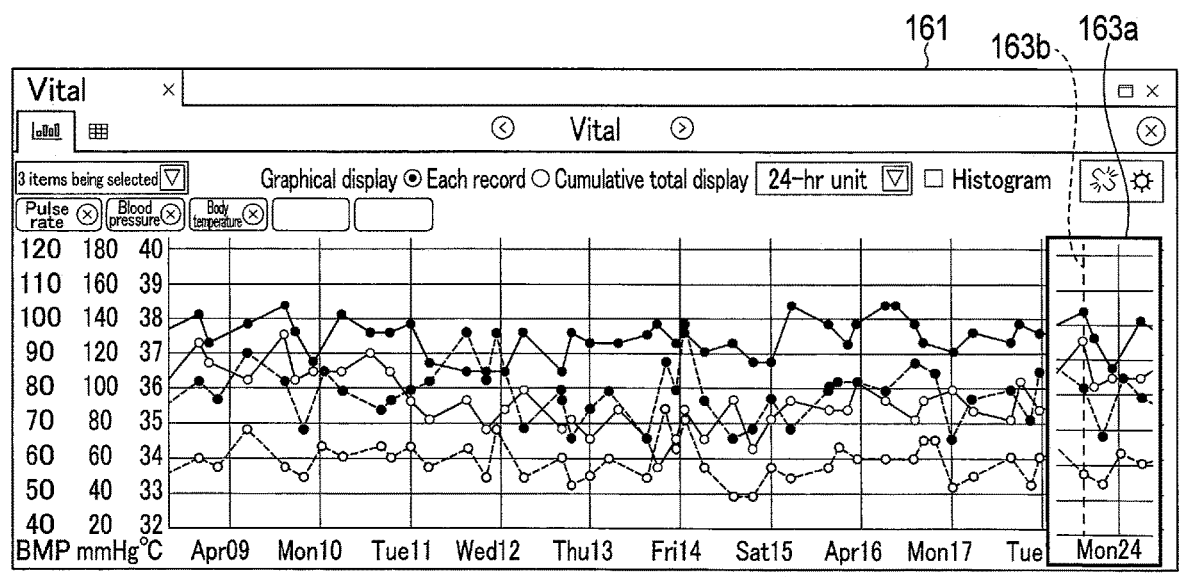
FIG. 16 is a view showing a display example of a vital sign information area including a preview area according to the embodiment.

FIG. 16 shows a display example of a vital sign information area including a preview area. As shown in FIG. 16, a vital sign information area 161 includes a preview area 163*a* displaying the data of vital sign information which is not displayed in the information display area. The preview area 163*a* displays both vital sign information concerning a designated date and time and an indicator 163*b* indicating a position corresponding to the designated date and time. Note that the preview area 163*a* is displayed at, for example, the position where the date and time corresponding to the data displayed in the information display area are closest to the designated date and time.

FIG. 17 shows a display example of a specimen examination information area including a preview area according to the embodiment. As shown in FIG. 17, a specimen examination information area 171 includes a preview area 173*a* displaying specimen examination data which is not displayed in the information display area. The preview area 173*a* displays both specimen examination information concerning a designated date and time and an indicator 173*b* indicating a position corresponding the designated date and time. Note that the preview area 173*a* is displayed at, for example, the position where the date and time corresponding to the data displayed in the information display area are closest to the designated date and time.

FIG. 18 shows a display example of a medical treatment record information area including a preview area according to the embodiment. As shown in FIG. 18, a medical treatment record information area 181 includes a preview area 183*a* displaying a comment which is not displayed in the information display area. The preview area 183*a* displays both the comment made by a doctor or nurse concerning a designated date and time and an indicator 183*b* indicating a position corresponding to the designated date and time. Note that preview area 183*a* is displayed at, for example, the position where the date and time corresponding to the comment displayed in the information display area are closest to the designated date and time.

FIG. 19 shows a display example of an image information area including a preview area according to the embodiment.

As shown in FIG. 19, an image information area 191 includes a preview area 193a displaying a thumbnail which is not displayed in the information display area. The preview area 193a displays both the thumbnail concerning a designated date and time and an indicator 193b indicating a position corresponding to the designated date and time. Note that preview area 193a is displayed at, for example, the position where the date and time attached to the thumbnail displayed in the information display area are closest to the designated date and time.

In other words, the preview area is arranged in the information display area and displays information concerning a designated date and time which is not included in the period displayed in the information display area. Displaying the preview area allows the operator to easily check information concerning the designated date and time existing outside the information display area.

Figure 20:
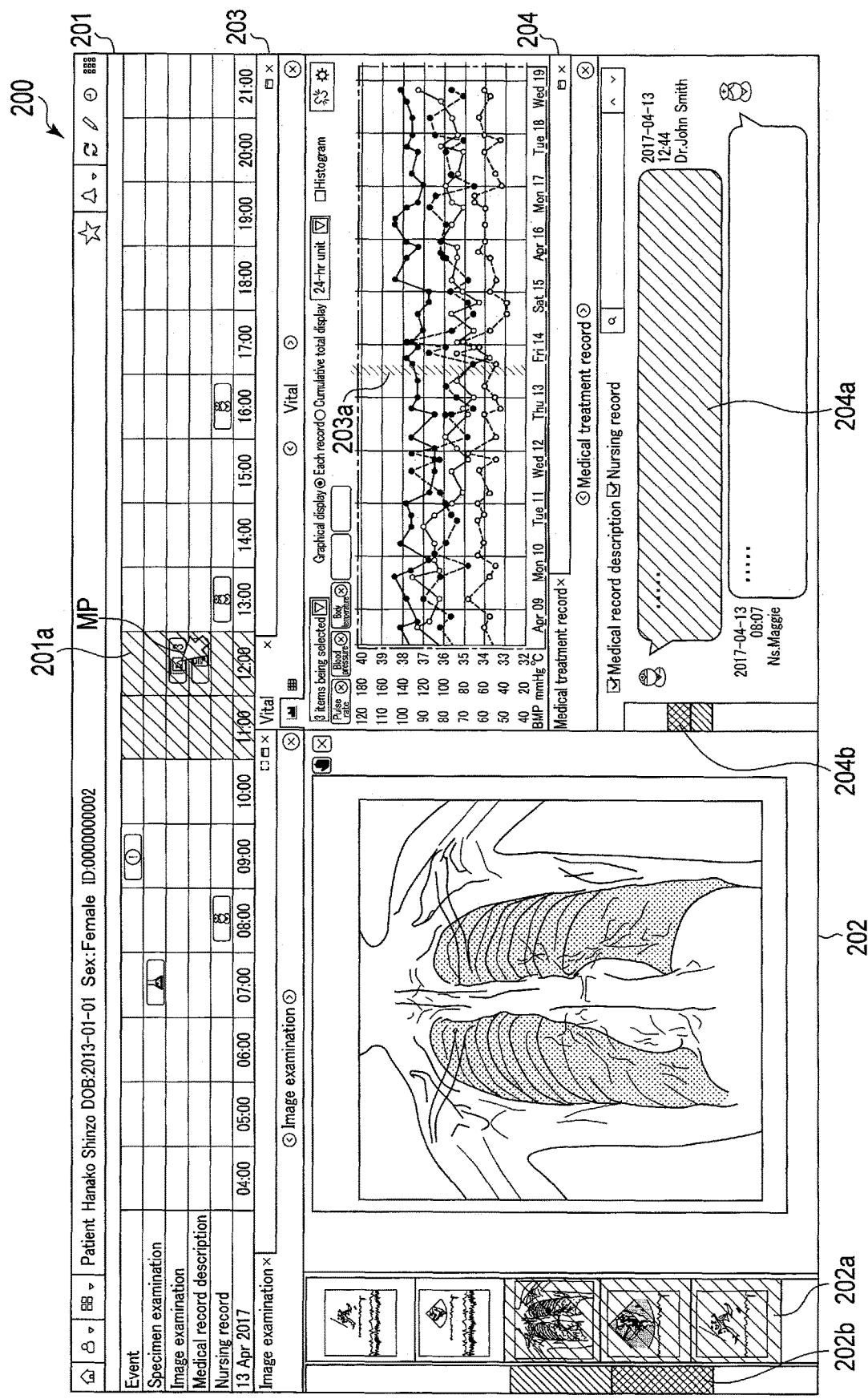
FIG. 20 is a view showing another example of the arrangement of the medical treatment screen displayed on the display in FIG. 2.

FIG. 20 shows another example of the arrangement of the medical treatment screen displayed on the display in FIG. 2. As shown in FIG. 20, a medical treatment screen 200 includes a timeline area 201 and medical treatment information area divided into an image information area 202, a vital sign information area 203, and a medical treatment record information area 204.

The information display area of the timeline area 201 includes an indicator 201a indicating the range of dates and times designated by the operator (designated date-and-time range "from 11:00 on Apr. 13, 2017 to 12:59 on Apr. 13, 2017").

The information display area of the image information area 202 includes an indicator 202a indicating a range corresponding to the designated date-and-time range. In addition, the navigation area (or the partial navigation area) of the image information area 202 includes an indicator 202b indicating a length corresponding to the designated date-and-time range.

The information display area of the vital sign information area 203 includes an indicator 203a indicating a range corresponding to the designated date-and-time range. Note that the information display area of the vital sign information area 203 may have a navigation area. In addition, the navigation area may include an indicator.

The information display area of the medical treatment record information area 204 includes an indicator 204a indicating a range corresponding to the designated date-and-time range. The navigation area (or the partial navigation area) of the medical treatment record information area 204 includes an indicator 204b indicating a length corresponding to the designated date-and-time range.

In summary, according to the embodiment, the indicator 202a, the indicator 202b, the indicator 203a, the indicator 204a, and the indicator 204b are automatically set (or displayed) in response to setting the indicator 201a first on the medical treatment screen 200.

According to the above description, a date-and-time range is designated in the information display area of the timeline area 201. However, this is not exhaustive, and a date-and-time range can be designated in any of the information display area of the image information area 202, the information display area of the vital sign information area 203, and the information display area of the medical treatment record information area 204. Alternatively, a date-and-time range may be designated in the navigation area attached to each information area.

FIG. 21 shows a display example of indicators according to the embodiment. FIG. 21 shows various types of indicators in an information display area 210a.

An indicator 211 is, for example, an indicator that is not indicating any date and time. More specifically, the indicator 211 indicates a broken line accompanying the mouse pointer position. Note that the indicators shown in FIGS. 1, 2, 3, 4, 5, 6, 7, 8, 9, 10, 11, 12, 13, 14, 15, 16, 17, 18, and 19 each are in a broken line form and regarded as an indicator designating a date and time for the sake of descriptive convenience.

An indicator 212 is, for example, an indicator indicating a designated date and time. The indicator 212 includes a solid line 212a, a slide portion 212b, and a cancellation portion 212c. The solid line 212a is replaced with, for example, a broken line (indicator 211) by the clicking operation of the mouse. The slide portion 212b is an operating portion that can move the indicator 211 in response to the drag-and-drop operation of the mouse. That is, the indicator 211 after movement and the indicator 211 before movement indicate different designated dates and times. The cancellation portion 212c is, for example, a button for returning to an indicator that is not designating any date and time in response to the clicking operation of the mouse.

An indicator 213 is, for example, an indicator that is designating a date-and-time range. The indicator 213 includes a date-and-time range 213a, a slide portion 213b, and a cancellation portion 213c. As the date-and-time range 213a, for example, a range corresponding to the moving width of the mouse pointer is designated with reference to the solid line (solid line 212a) in response to the drag-and-drop operation of the mouse. The slide portion 213b and the cancellation portion 213c are respectively equivalent to the slide portion 212b and the cancellation portion 212c.

Note that the form of each indicator is not limited to the above form. In addition, only the solid line 212a and the date-and-time range 213a may be simply called indicators.

FIGS. 22A, 22B, and 22C exemplarily show an indicator moving method according to the embodiment. The operator designates a date and time by moving the mouse pointer MP. At this time, an indicator 221 moves accompanying the mouse pointer MP. The operator designates a date and time by clicking a position where he/she wants to designate a date and time. Because the operator designates a date and time, the indicator 221 is replaced with a slid line 222a and displayed. The operator can move a moving portion 222b (indicator) by dragging and dropping the moving portion 222b in the direction indicated by an arrow AR1 with the mouse pointer MP.

FIGS. 23A and 23B exemplarily show an indicator range selection method according to the embodiment. The operation of designating a date and time is the same as that shown in FIG. 22A. The operator designates a date-and-time range by dragging and dropping a solid line 232a in the direction indicated by an arrow AR2 with the mouse pointer MP. Because the operator has designated a date and time, the solid line 232a is replaced with a date-and-time range 233a and displayed.

FIGS. 24A and 24B exemplarily show a method of moving an indicator upon range selection according to the embodiment. The operation of designating a date and time is the same as that in FIG. 23B. The operator can move a date-and-time range 243a (indicator) by dragging and dropping a moving portion 242b in the direction indicated by an arrow AR3 with the mouse pointer MP.

FIG. 25 shows a display example of a medical treatment recording information area displaying an indicator on a comment according to the embodiment. As shown in FIG.

25, a medical treatment recording information area 251 includes an information display area 251a and a navigation area.

The information display area 251a displays comments made by a doctor and a nurse concerning a specific patient over a certain period. More specifically, the information display area 251a displays five comments including a comment 253a, a comment 253b, and a comment 253c. The comment 253b includes an indicator 251b indicating a position corresponding to the designated date and time.

FIG. 26 exemplarily shows a method of calculating the display position of the indicator in FIG. 25. The comment 253a is associated with date and time A (for example, "12:44 on Apr. 13, 2017") and has a pixel count α corresponding to a commend width 262a. The comment 253b is associated with date and time B (for example, "08:07 on Apr. 13, 2017") and has a pixel count β corresponding to a comment width 262b. The comment 253c is associated with date and time C (for example, "10:37 on Apr. 12, 2017") and has a pixel count γ corresponding to a comment width 262c.

Assume that when indicator 251b is displayed on the comment 253b, a designated date and time are a date and time included between date and time AB between date and time A and date and time B and date and time BC between date and time B and date and time C. A pixel count X of a pixel width 261 from the lower portion of the comment 253b to the display position of the indicator 251b is calculated by using for example, equation (1):

$$\text{pixel count } X = \text{pixel count } \beta \times \{(\text{designated date and time} - \text{date and time } BC)/(\text{date and time } AB - \text{date and time } BC)\} \quad (1)$$

Displaying an indicator on a comment allows the operator to easily grasp a specific comment, of the comment and its adjacent comments, to which a designated date and time are closer. Note that when the designated date and time coincide with the date and time associated with a comment, an indicator whose color has been changed may be displayed on the comment.

Figure 27:
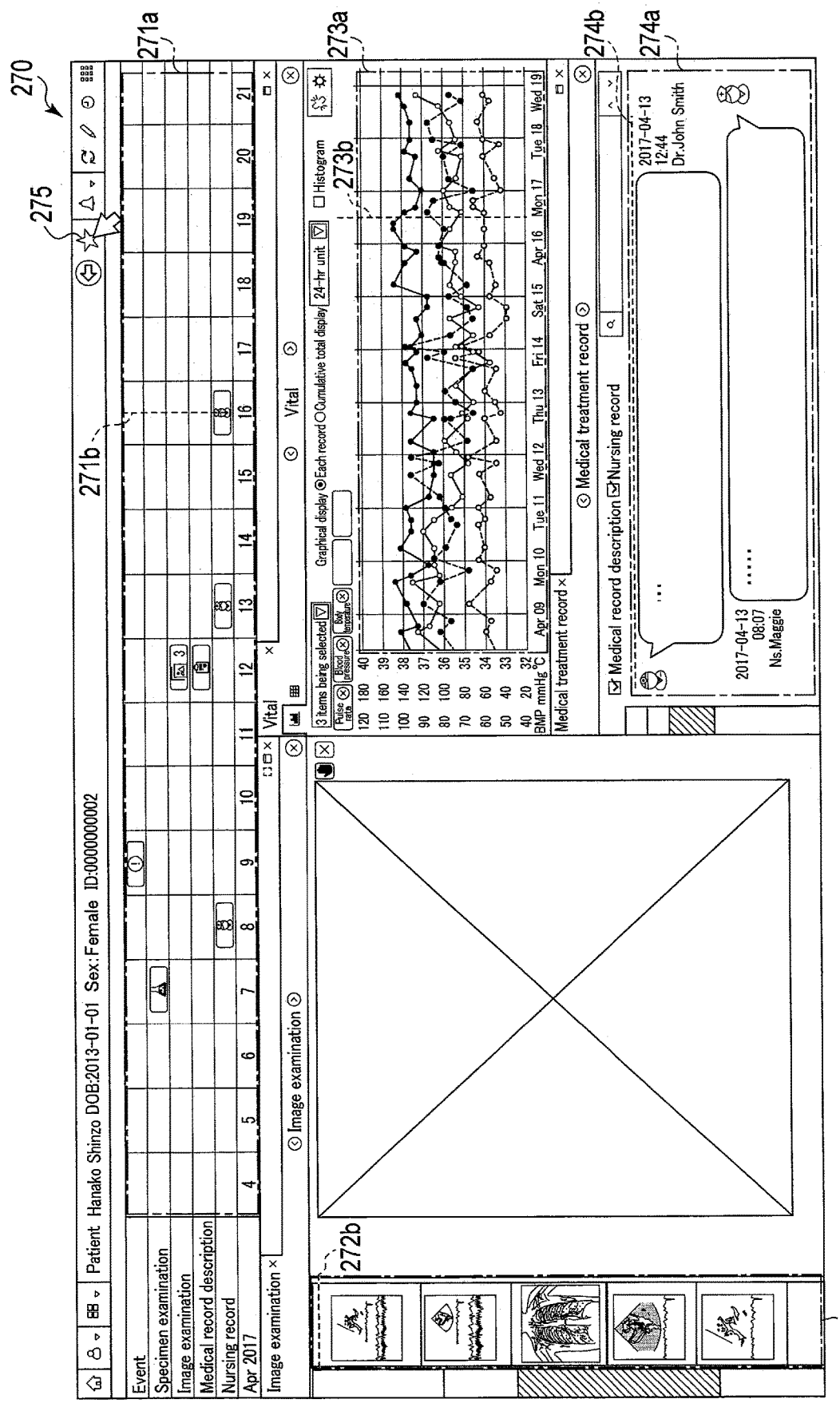
FIG. 27 is a view showing another example of the arrangement of the medical treatment screen displayed on the display in FIG. 2.

FIG. 27 shows another example of the arrangement of the medical treatment screen displayed on the display in FIG. 2. As shown in FIG. 27, a medical treatment screen 270 includes an information display area 271a of a timeline area, an information display area 272a of an image examination area, an information display area 273a of a vital sign information area, an information display area 274a of a medical treatment record information area, and a positioning button 275.

The information display area 271a includes an indicator 271b indicating the position of the date and time designated by the operator (designated date and time "Apr. 16, 2017"). The information display area 272a includes an indicator 272b indicating a position corresponding to the date and time closest to the designated date and time. The information display area 273a includes an indicator 273b indicating a position corresponding to the designated date and time. The information display area 274a includes an indicator 274b indicating a position corresponding the date and time closest to the designated date and time.

Selecting the positioning button 275 on the medical treatment screen 270 upon selection of a designated date and time makes it possible to locate each indicator in the center of each information display area.

Figure 28:
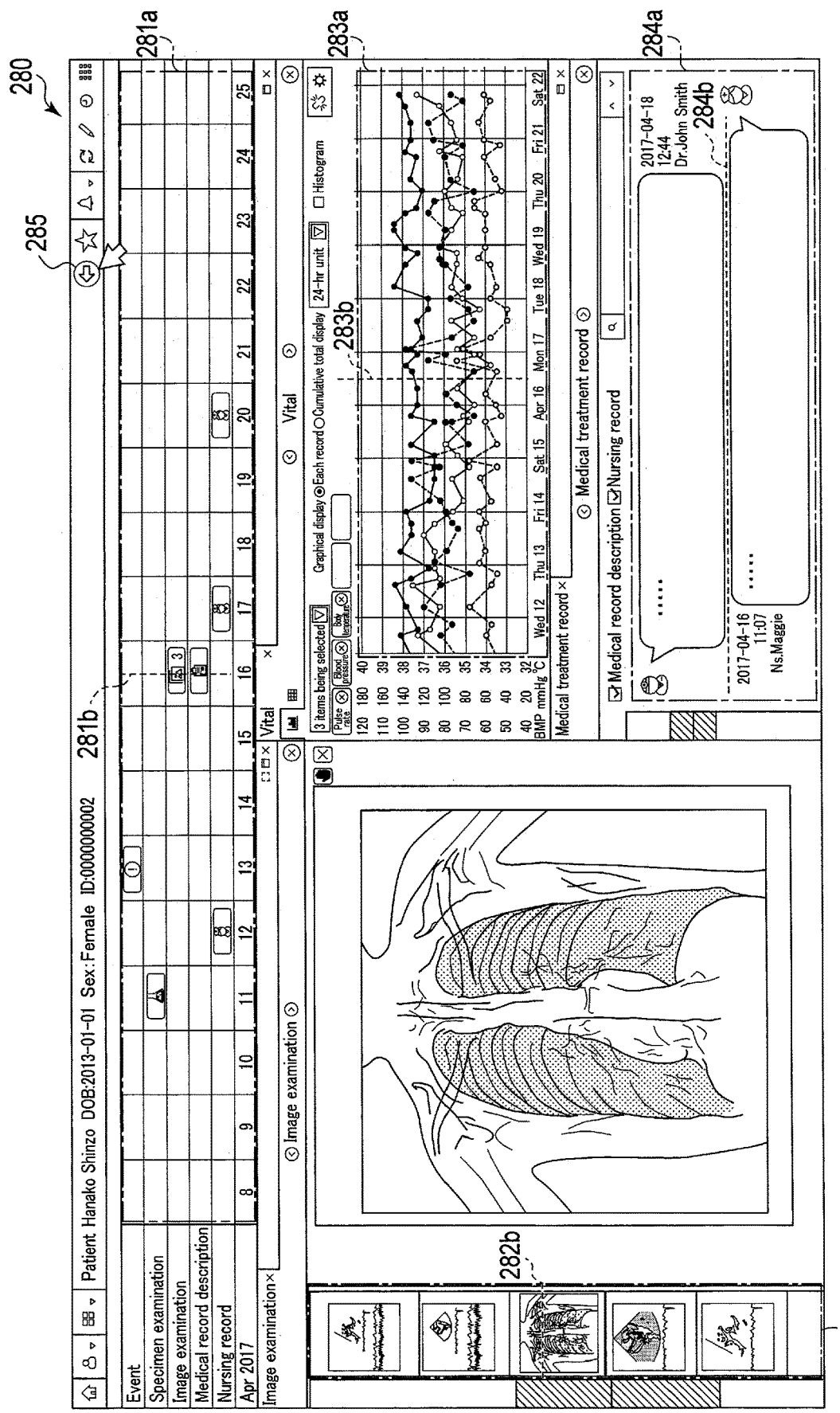
FIG. 28 is a view showing an example of the arrangement of the medical treatment screen in FIG. 27 upon execution of positioning.

FIG. 28 shows an example of the arrangement of the medical treatment screen in FIG. 27 after the execution of positioning. As shown in FIG. 28, a medical treatment screen 280 includes an information display area 281a of a timeline area, an information display area 282a of an image examination area, an information display area 283a of a vital sign information area, an information display area 284a of a medical treatment record information area, and a button 285.

Upon execution of positioning, an indicator 281b corresponding to the indicator 271b is displayed in the center of the information display area 281a. Likewise, an indicator 282b associated with the indicator 272b is displayed in the information display area 282a. An indicator 283b corresponding to the indicator 273b is displayed in the center of the information display area 283a. An indicator 284b associated with the indicator 274b is displayed in the information display area 284a.

Selecting the button 285 on the medical treatment screen 280 upon execution of positioning makes it possible to return to the medical treatment screen 270 before the execution of positioning. This allows the operator to see the medical treatment screens before and after positioning by switching the screens.

According to the embodiment described above, the medical information display apparatus, which causes the display to display the first area displaying the first medical information over the first period and the second area displaying the second medical information over the second period, acquires the time information designated in the first area, decides a position associated with the time information designated in the second area based on the designated time information and the second period, and displays the decided position and the second medical information in the second area.

The medical information display apparatus can, therefore, display the date and time designated in the first area in interlocking with a position associated with the date and time in the second area, and hence can display medical information in a plurality of areas so as to allow the operator to easily understand the association between the information. In addition, this medical information display apparatus can shorten the time taken to refer to target data in medical treatment data having a complicated relationship, thereby reducing the risk of overlooking the complicated relationship.

According to the embodiment, the medical information display apparatus decides a position based on whether designated time information is included in the second period. This allows the medical information apparatus to change the display of time information depending on whether designated time information is included in the display range of the second area.

According to the embodiment, the medical information display apparatus decides a position corresponding to designated time information when the designated time information is included in the second period. This allows the medical information display apparatus to decide a position corresponding the designated time information in the display range of the second area.

According to the embodiment, when designated time information is not included in the second period, the medical information display apparatus decides a position corresponding to time information closest to the designated time information in the second period. This allows the medical information display apparatus to notify the operator that the designated time information exists outside the display range of the second area.

According to the embodiment, the medical information display apparatus includes, in the second area, the navigation area corresponding to a period including at least the second period and the partial navigation area arranged in the navigation area and corresponding to the second period, and displays the navigation area including an indicator indicating the decided position in the second area. This allows the medical information display apparatus to notify the operator of how much data exists outside the display range of the second area.

According to the embodiment, the medical information display apparatus includes, in the second area, the information display area displaying the second medical information over the second period and the preview area displaying information associated with designated time information which is arranged in the information display area and is not included in the second period, and displays, in the second area, the preview area including information associated with the designated time information which is not included in the second period. This allows the medical information display apparatus to notify the operator of data existing outside the display range of the second area without changing the second period.

According to the embodiment, the medical information display apparatus switchably displays, on the display, the first and second areas before positioning and the first and second areas after positioning. This allows the medical information display apparatus to present the medical treatment screens before and after positioning upon switching the screens.

In addition, according to the embodiment, for example, the medical information display apparatus displays the first medical information over the first period along the first time axis and the second medical information over the second period along the second time axis, acquires time information at a designated time point or in a designated range in the first period concerning the first medical information displayed, decides a position on the second time axis which corresponds to the time information, and displays an indicator indicating the decided position in the area displaying the second medical information.

According to the embodiment, the medical information display apparatus decides a position on the second time axis based on whether time information is included in the second period. If the time information is included in the second period, the medical information display apparatus decides a position in the second period which corresponds to the time information. If the time information is not included in the second period, the medical information display apparatus decides a position in the second period which corresponds to time information in the second period which is closest the time information. Alternatively, if the time information is not included in the second period, the medical information display apparatus displays medical information corresponding to the time information as a preview in the above area.

According to the embodiment, the medical information display apparatus displays the first medical information in another area different from the above area.

The above area includes a navigation area corresponding to a period including at least the second period and a partial navigation area arranged in the navigation area and corresponding to the second period. In this case, the medical information display apparatus displays another indicator indicating a position on the second time axis in the navigation area displayed regardless of the arrangement position of the partial navigation area.

In addition, the above area includes an information display area that displays the second medical information and an indicator. In this case, if time information is not included in the second period, the medical information display apparatus arranges and displays a preview area displaying medical information corresponding to the time information in the information display area.

According to the embodiment, the medical information display apparatus displays a position on the first time axis and a position on the second time axis, which correspond to time information, upon positioning the positions so as to make them coincide with the center of the another area and the center of the above area. In addition, the medical information display apparatus switchably displays the display state of the another area and the above area before positioning and the display state of the another area and the above area after positioning.

According to the embodiment, the medical information apparatus acquires a cancel instruction to cancel time information and displays the above area upon removing the indicator from the area in accordance with the acquired cancel instruction.

When the operator needs to select a date and time in consideration of information on a plurality of panels in different display forms (when, for example, being interested in a specific relationship between medication and a specimen examination), the conventional medical information display apparatus needs to search for a target date and time by repeating display switching processing on some panels, resulting in a complex operation. In contrast to this, the medical information display apparatus according to the embodiment can complete a similar operation by only deciding a date and time on a given panel. This facilitates operations as compared with the prior art.

According to at least one embodiment described above, it is possible to display medical information in a plurality of areas so as to allow easy understanding of the association between the medical information.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical information display apparatus, comprising:
   a memory configured to store a plurality of medical information in association with corresponding dates and times; and
   processing circuitry configured to:
   cause a display to display an interface having a first area and a second area distinct from the first area, and display, along a first time axis in the first area representing a first period, a plurality of selectable icons, each icon corresponding to respective first medical information and being arranged in the first area at a location indicating a time point or time range at which the respective plurality of first medical information was obtained;
   cause the display to display second medical information over a second period along a second time axis in the second area;
   receive a selection of an icon, of the displayed plurality of icons, by a user;

acquire, from the memory, time information at a particular time point or in a particular time range in the first period corresponding to the selected icon;

cause the display to display, at a first position, a first indicator indicating the acquired time information in the first area displaying the plurality of selectable icons;

determine a second position on the second time axis that corresponds to the time information of the first indicator acquired from the memory; and cause the display to display a second indicator indicating the determined second position in the second area displaying the second medical information.

2. The apparatus according to claim 1, wherein the processing circuitry is further configured to determine the second position based on whether the acquired time information is included in the second period.

3. The apparatus according to claim 2, wherein when the acquired time information is included in the second period, the processing circuitry is further configured to determine the second position in the second period that corresponds to the acquired time information.

4. The apparatus according to claim 2, wherein when the acquired time information is not included in the second period, the processing circuitry is further configured to determine the second position in the second period that corresponds to particular time information in the second period that is closest to the acquired time information.

5. The apparatus according to claim 2, wherein when the acquired time information is not included in the second period, the processing circuitry is further configured to display medical information corresponding to the acquired time information as a preview in the second area.

6. The apparatus according to claim 1, wherein the processing circuitry is further configured to display the plurality of icons in the first area, which is different from the second area.

7. The apparatus according to claim 6, wherein the second area includes a navigation area corresponding to a period including at least the second period and a partial navigation area arranged in the navigation area and corresponding to the second period, wherein the processing circuitry is further configured to display another indicator indicating a position on the second time axis in the navigation area displayed regardless of a displayed position of the partial navigation area relative to a display of the navigation area.

8. The apparatus according to claim 6, wherein the second area includes an information display area that displays the second medical information and the second indicator, wherein when the acquired time information is not included in the second period, the processing circuitry is further configured to arrange and display a preview area displaying medical information corresponding to the acquired time information in the information display area.

9. The apparatus according to claim 6, wherein the processing circuitry is further configured to display the first indicator on the first time axis and the second indicator on the second time axis, each corresponding to the acquired time information so as to make the first and second positions respectively coincide with a center of the first area along the first time axis and a center of the second area along the second time axis.

10. The apparatus according to claim 9, wherein the processing circuitry is further configured to switchably display a display state of the first area and the second area before positioning, and a display state of the first area and the second area after positioning.

11. The apparatus according to claim 1, wherein the processing circuitry is further configured to:

acquire a cancel instruction to cancel the acquired time information; and display the second area upon removing the indicator from the second area in accordance with the cancel instruction.

12. The medical information display apparatus of claim 1, wherein the processing circuitry is further configured to display the second indicator in the second area, which is in a different window from a window in which the first indicator is displayed.

13. The medical information display apparatus of claim 1, wherein the processing circuitry is further configured to cause the display to display the first and second areas having the first and second time axes, respectively, the first time axis having a different scale than that of the second time axis.

* * * * *